United States Patent [19]

Hoffman et al.

[11] Patent Number: 4,912,032
[45] Date of Patent: Mar. 27, 1990

[54] METHODS FOR SELECTIVELY REACTING LIGANDS IMMOBILIZED WITHIN A TEMPERATURE-SENSITIVE POLYMER GEL

[75] Inventors: Allan S. Hoffman; Nobuo Monji, both of Seattle, Wash.

[73] Assignee: Genetec Systems Corporation, Seattle, Wash.

[21] Appl. No.: 948,377

[22] Filed: Dec. 31, 1986

Related U.S. Application Data

[63] Continuation-in-part of Ser. No. 853,697, Apr. 17, 1986, abandoned, and a continuation-in-part of Ser. No. 854,831, Apr. 28, 1986, Pat. No. 4,780,409, which is a continuation-in-part of Ser. No. 729,510, May 2, 1985, abandoned.

[51] Int. Cl.$^4$ .................... G01N 33/00; G01N 33/543
[52] U.S. Cl. ............................................ 435/7; 435/6; 436/518; 436/519; 436/539; 436/540; 436/824
[58] Field of Search ............... 435/7, 6; 436/501, 519, 436/539, 540, 824, 827, 518

[56] References Cited

U.S. PATENT DOCUMENTS

| | | | |
|---|---|---|---|
| 3,421,893 | 1/1969 | Taylor | 430/215 |
| 3,767,790 | 10/1973 | Guttag . | |
| 3,859,169 | 1/1975 | O'Driscoll et al. | 435/182 |
| 3,975,350 | 8/1976 | Hudgin et al. . | |
| 4,070,348 | 1/1978 | Kraemer et al. . | |
| 4,360,358 | 11/1982 | Sharma | 436/509 |
| 4,364,385 | 12/1982 | Lossef . | |
| 4,530,900 | 7/1985 | Marshall | 436/536 X |
| 4,711,840 | 12/1987 | Nowinski et al. | 436/539 X |
| 4,749,647 | 6/1988 | Thomas et al. | 436/539 X |
| 4,780,409 | 10/1988 | Monji et al. . | |

Primary Examiner—Robert J. Warden
Assistant Examiner—Richard Wagner

[57] ABSTRACT

Methods for delivering substances into, removing substances from, or reacting substances with a selected environment utilizing polymer gels or coatings characterized by a critical solution temperature (CST) are disclosed. The CST as well as the pore structure, pore size, pore distribution, and absorbing capacity of the gel may be selectively controlled. The substances may be physically or chemically immobilized within the polymer gels. In addition, a method for altering the surface wettability of CST polymers is also disclosed.

53 Claims, 17 Drawing Sheets

EFFECT OF TEMPERATURE ON WATER CONTENTS OF LOST HYDROGELS

TEMPERATURE DEPENDENCE OF SPECIFIC ACTIVITY (FIRST RUN)

• MN-0-f
○ MN-1-f

TEMPERATURE DEPENDENCE OF SPECIFIC ACTIVITY (THIRD RUN)

- MN-0-f
- MN-1-f

TEMPERATURE DEPENDENCE OF SPECIFIC ACTIVITY (THIRD RUN)

• MN-O-C
o MN-1-C

GRAFTING NIPAAm/AAm MIXTURES TO SILASTIC

Dose: 0.68 Mrad; air atmosphere

Solutions: 100 mM Cu(NO$_3$)$_2$ in D.I. water + 10% (wt) total monomer

EFFECT OF TEMPERATURE ON WATER CONTENTS OF SILICONE RUBBER FILMS GRAFTED BY NIPAAm / AAm MIXTURES

Dose: 0.68 Mrad; air atmosphere

Solutions: 100 mM Cu(NO$_3$)$_2$ in D.I. water + 10% (wt) total monomer

| Film No. | NIPAAm / AAm |
| --- | --- |
| 1 | 0 / 10 |
| 2 | 2 / 8 |
| 3 | 4 / 6 |
| 4 | 6 / 4 |
| 5 | 8 / 2 |
| 6 | 10 / 0 |

METHODS FOR SELECTIVELY REACTING LIGANDS IMMOBILIZED WITHIN A TEMPERATURE-SENSITIVE POLYMER GEL

CROSS-REFERENCE TO RELATED APPLICATIONS

This application is a continuation-in-part of U.S. application Ser. Nos. 853,697, filed April 17, 1986, now abandoned, and 854,831, filed April 28, 1986, now U.S. Pat. No. 4,780,409 which is a continuation-in-part of U.S. application Ser. No. 729,510, filed May 2, 1985, now abandoned.

TECHNICAL FIELD

The present invention relates generally to methods for delivering substances into, removing substances from, or reacting substances with a selected environment in order to effect a desired purpose, utilizing polymer gels or coatings exhibiting either an upper or a lower critical solution temperature.

BACKGROUND ART

A number of polymers undergo a phase separation in response to a change in environmental conditions, such as solution pH, ionic strength or temperature. For instance, some soluble polymers become insoluble when the solution temperature is changed only a few degrees. These polymers are said to possess a critical solution temperature (CST). A polymer possessing a lower critical solution temperature (LCST) becomes insoluble when the temperature of the solution is increased through a particular narrow temperature range. Conversely, a polymer possessing an upper critical solution temperature (UCST) becomes insoluble when the temperature of the solution is decreased through a particular narrow temperature range.

Polymers capable of phase changes in response to temperature changes have been described by Taylor in U.S. Pat. No. 3,421,892 for use in controlling a process relating to film developing. In Taylor, a layer of polymer changes permeability as a function of temperature. The polymers are layered between supporting color-sensitive silver halide layers and are selected and designed to control the diffusion rate of chemical dyes in order to improve color isolation and process speed. The polymer layers are substantially dye-permeable only in the hydrated state. This results in an overall film development process that is substantially independent of temperature. Suitable polymers for use within the layers are identified as polyvinyl amides and, most preferably, polyacrylamides, including a variety of N-substituent groups. The N-substituents are selected, balancing hydrophilic groups that cause swelling as a function of the solubility of that group in a given solvent with hydrophobic groups which modulate the swelling so that at some definite ratio of hydrophilic to hydrophobic groups, the resultant compound will have the desired temperature-inverting properties. The Taylor polymers are designed to avoid extreme inverse temperature characteristics, since the purpose of the barrier is to be functionally compatible with the temperature-permeation properties of the rest of the photosensitive unit. One disadvantage of the polymers disclosed by Taylor is that they are not in a cross-linked form, and therefore require a supporting structure. Thus, they cannot conveniently be used as a permeation barrier independent of a solid-phase support.

Lim, in U.S. Pat. No. 4,407,957, describes suspending cells in a polyalginate solution and adding the suspension dropwise into a solution containing calcium ions that gels the alginate and encapsulates the cells. A membrane is deposited through interaction of a polymer which has an opposite charge (positive charge) with the gel particle itself. This interaction results in a polyelectrolyte complex skinned membrane on the gel surface. The gel entrapping the cells may be redissolved by exchanging the calcium ions in the gel with a $Na^+$ ion, thus promoting diffusion of metabolites through the ionically "cross-linked" membrane encapsulating the cells. Lim describes injecting such a gel material, including encapsulated insulin into a mammalian body, for example. The gel is said to release insulin into the body over time as it diffuses through the gel pores.

Cussler, in U.S. Pat. No. 4,555,344, describes using a cross-linked ionic polymer gel, such as partially hydrolyzed polyacrylamide or dextran, to selectively absorb a low molecular weight solvent and solute from a solution that includes higher molecular weight components in the solution. The gel is introduced into the solution in a shrunken state. A pH change or a change in composition of the solution is required to cause the gel to rapidly swell in volume, absorbing low-molecular weight solvent and solute.

Graham, in U.S. Pat. No. 4,584,188, describes gels comprising a polymerizable cyclic (thio) ether and a hydrophilic homo- or copolymer. A temperature change is required for expelling or releasing from the gel an active substance previously absorbed from a solution.

A limitation to date regarding the use of polymer gels that change phases in response to a change in environmental conditions has been that separations from or deliveries to solutions have been substantially nonspecific. Both the Cussler and the Graham inventions rely upon a temporary physical entrapment of the solution or solvent within the gel. That is, a CST gel, for example, in response to a change in temperature through the CST absorbs a liquid to which it has been exposed. The solution is absorbed by the gel nonspecifically, only excluding molecules too large for its pore structure.

Consequently, there exists a need in the art for an improved system for controlling biological or chemical reactions in selected environments by providing methods of separating certain desired substances from a solution, delivering certain selected substances to, or exposing certain selected substances to a desired environment, which methods are readily and efficiently controllable. The present invention fulfills this need and further provides other related advantages.

DISCLOSURE OF THE INVENTION

Briefly stated, the present invention provides methods for delivering substances of interest to an environment sought to be affected. Delivered substances may include acids, bases, dyes, drugs, reactants, catalysts, and affinity binding components, as well as many other useful substances that impact the environment in a desired manner. An additional aspect of the present invention is directed toward a method of removing such substances from selected environments. A related aspect of the present invention provides a method for exposing substances to a selected environment. Briefly, polymer gels are disclosed that selectively expose such an environment to a reactive substance of interest immobilized within the gel.

The method for delivering a desired substance into a selected environment utilizes polymer gels characterized by a critical solution temperature (CST). The "critical solution temperature," as used herein, is the temperature at which the polymer gel will shrink or swell, releasing or absorbing solvent, including a substance of interest. For delivering a desired substance, the substance is incorporated into the gel while the gel is generally in a solvated, swollen state. The substance may then be introduced into the selected environment by adjusting the temperature of the polymeric gel/substance sufficiently near the critical solution temperature to cause the gel to desolvate, thereby releasing the desired substance into the environment. It may also be introduced into the environment by drying or removing the solvent from the gel which contains the previously imbibed substance to be released, before later exposing to an environment above or below its CST.

In a typical procedure, the polymer gel (characterized by a critical solution temperature) is contacted with the substance desired to be delivered to the selected environment. The temperature of the polymer gel is adjusted, whereby the gel absorbs the substance. The gel is placed into contact with the environment of interest and the temperature adjusted, whereby the gel releases the substance into the environment. As noted above, the initial temperature of the polymer gel may be such that it is in a partially or totally desolvated state when contacted with the substance to be absorbed and subsequently delivered. Alternatively, the polymer may be in a solvated state, contacted with the substance, and the temperature cycled, causing the polymer to desolvate and, upon reversing the temperature, to solvate, absorbing the desired substance.

The substance may be incorporated in the polymer by physical absorption or entrapment within the pores of the gel. The substance may also be incorporated or entrapped via molecular entanglements and interactions within denser regions of the polymer gel, typically by means of secondary (ionic, polar, hydrophobic, etc.) forces binding the substance to the polymer. In addition, the substance may also be bound to the gel matrix by means of labile, primary covalent bonds. A labile bond arrangement is useful in drug delivery, wherein, for example, an LCST gel polymer at 37° C. is desolvated and includes the drug bound to the polymer by means of the labile bond. The gel is injected into the body in the form of gel particles or microspheres including the drug. The desired delivery area is then cooled to 35° C., which causes the gel to swell and absorb surrounding aqueous solution, whereupon the drug polymer bond is broken and the drug released.

The pore structure of the CST polymer may be adjusted by a number of means to selectively retain a desired substance within the gel. Pore structure, and hence, the amount of substance released and release rate are selectively controlled by adjusting the composition and/or concentration of monomers in the synthesis mixture employed to form the gel. Also, adjusting the amount and composition of cross-linking agent employed to synthesize the gel allows one to selectively adjust the pore size to retain a particular identified substance of interest. In a preferred method, the polymer may be N-isopropyl acrylamide (NIPAAm) and its copolymers with acrylamide or other N-substituted acrylamides, and the cross-linking agent methylene bis-acrylamide. Pore size is also adjustable by selecting the solvent in which the polymer is synthesized. For instance, the synthesis may be carried out in aqueous or organic solvents or mixtures thereof.

In addition to the synthesis of self-supporting gel systems, one may also envisage immobilization of such gels as coatings onto other polymeric supports. In particular, the well-known processes of radiation grafting, photochemical grafting, plasma gas discharge polymer deposition, chemically initiated grafting (such as ozone initiation) and so on, may be utilized to form grafted LCST polymeric gels onto the surface of a different polymeric support. The polymeric support could be activated to form free radicals on its backbone in the presence of the hydrogel of the LCST gel, or it may be preactivated either in inert atmosphere or an air atmosphere to provide active sites which are capable of initiating the free radical polymerization of the LCST gel on the surface of the polymer substrate ("Radiation Chemistry of Monomer and Polymeric Systems" by Chapiro, Interscience Press, 1962). Such polymer substrates include a wide variety of polymeric compositions. Furthermore, if the monomers are preswelled into the matrix of the substrate polymer, then one may subsequently initiate a radiation polymerization of the LCST gel within the second substrate polymer, and form an interpenetrating network of the LCST hydrogel within a different polymeric support.

In particularly preferred embodiments of the methods set forth herein, the polymer gel is characterized by a lower critical solution temperature (LCST). The LCST polymer gel may include a polymer such as poly(substantially hydrophobic N-substituted acrylamides or methacrylamides), hydroxy alkyl celluloses, polyoxazolidones, polyvinylmethylether, polyethylene oxide, polymethacrylic acid, or copolymers thereof, including variations in the polar or hydrophobic components of all of these polymers.

The methods described herein may also include a polymer gel that is characterized by an upper critical solution temperature (UCST). Such a polymer gel may include a polymer such as polyacrylic acid, polymethacrylamide, or polyvinyl alcohol, and copolymers thereof.

The methods described herein, in addition to delivery, allow the separation of a desired substance from a solution. Typically, the procedure is initiated by introducing a dry or shrunken polymer gel characterized by a critical solution temperature (as described above) into the solution containing the desired substance. Utilizing the CST character of the polymer, one can adjust the temperature of the gel/solution sufficiently to cause the gel to swell and absorb the desired substance. As with the delivery method, the process may utilize either a lower or upper critical solution temperature polymer of the type described above.

This separation method is particularly useful in bioseparations, wherein the polymer gel includes a first component of a binding pair bound physically or chemically to the polymer. The polymer gel/binding component is contacted with a solution that contains the second component of the binding pair. This mixture is then incubated at a temperature sufficient to cause the polymer gel/first binding component to absorb liquid from the solution containing the second binding component, thereby allowing the second binding component to specifically bind to the first binding component. The solution is then heated or cooled to cause the gel to shrink and desolvate whereby the gel releases the remaining solution and retains the bound binding pairs.

The polymer gel/binding pair may then be transferred to an eluting solution having the capability of breaking the bond between the binding components and the polymer gel. The temperature is adjusted, causing the gel to swell, whereupon the binding pair is separated from the gel. The temperature is then readjusted to desolvate the gel releasing the freed binding pair from the gel pore structure.

Depending upon the substance of interest, the binding pair may be an affinity pair, or, alternatively, the binding pair may be a less-specific binding pair. Suitable affinity binding pairs include an antibody which binds to an antigen or hapten of interest. As discussed in detail below, other ligand binding pair components include lectin and polysaccharide or glycoprotein; DNA, RNA, (single- or double-stranded) with complementary DNA, RNA or oligonucleotides, or proteins or steroids; ion with chelator, ionophore complexer; and stable-free radical with free radicals. In addition, a receptor may be bound to the polymer gel that is designed to bind with a hormone, vitamin, lectin, drug, dye, or lipid binding partner in solution. As more fully set forth below, suitable ligands for immobilization within the gel may also include a nonspecific binding component that will react with a binding partner of interest in an environment.

Another important aspect of the methods of the present invention is the capacity to control chemical or biological reactions. Typically, a reactant composition that causes a desired effect upon an environment of interest is first immobilized within a CST gel. The reaction or effect upon the environment is then controlled by heating or cooling the gel above and/or below its respective CST. Such reactant compositions may include enzymes, catalysts, oxidizing agents, reducing agents, acids, bases, or free radical transfer groups. A particularly useful method includes binding an enzyme within the polymer gel, adjusting the temperature of the polymer gel/enzyme sufficiently to allow solution containing the enzyme substrate from the environment of interest to contact the enzyme, thereby initiating and catalyzing the reaction of interest. Further adjustment of the temperature allows one to control the rate of reaction. Reversing the temperature beyond a CST will cause the polymer gel to shrink, closing off contact of the reactant with the solution, thereby substantially slowing down or terminating the reaction. Alternatively, the reaction may be selectively controlled by gradually causing the polymer gel to shrink. In addition, through use of a combination of temperature and controlled pore size, one can selectively eliminate access of different sized molecules as the temperature is raised or lowered.

These and other aspects of the present invention will become evident upon reference to the following detailed description and attached drawings.

BEST MODE FOR CARRYING OUT THE INVENTION

Figure 1:
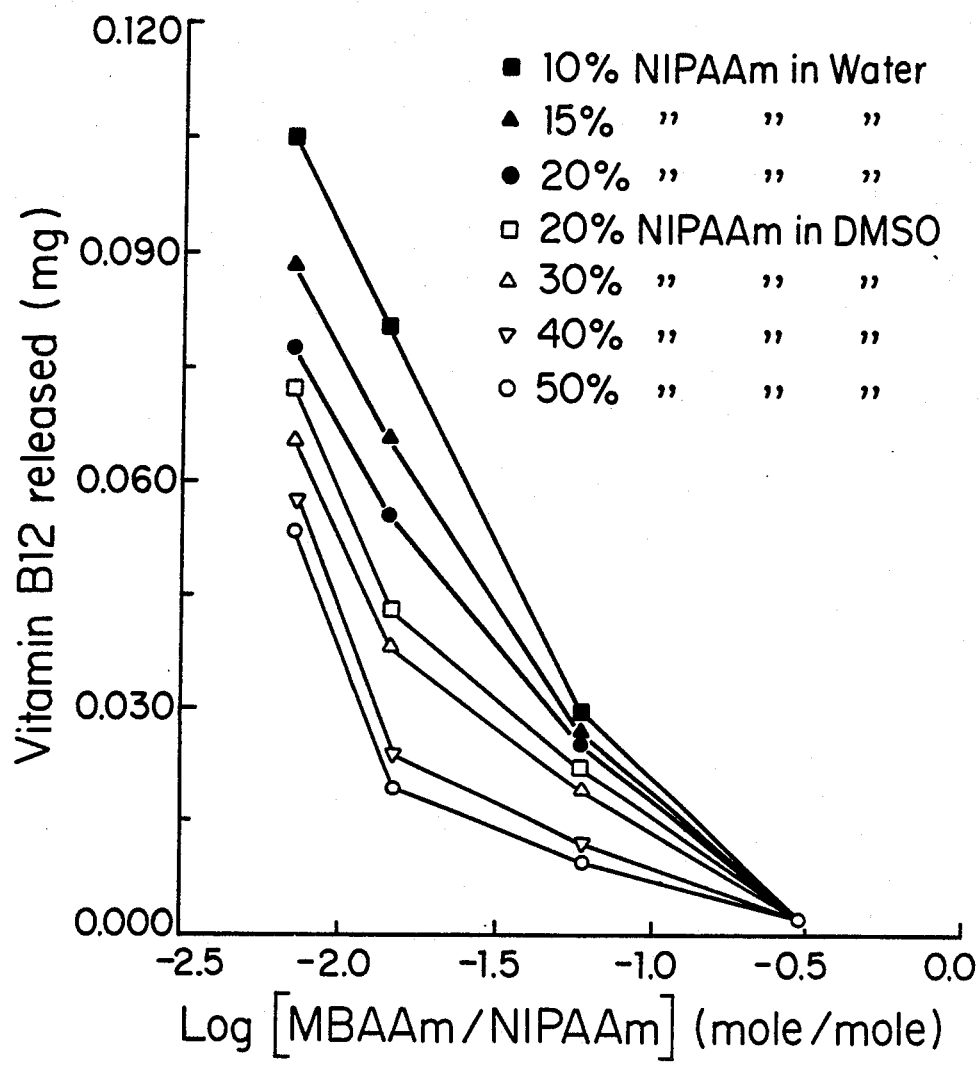
FIG. 1 presents vitamin $B_{12}$ delivery as a function of cross-linker/monomer ratio, for indicated solution, monomer and solvent composition used to synthesize poly-NIPAAm gels.

The methods of the present invention utilize, as a principal component, a polymer that is characterized by a capability of precipitating from an aqueous solution within a narrow temperature range. The temperature at which polymer precipitation is initiated is often termed the "critical solution temperature" (CST) for the polymer.

The CST polymer of interest may be copolymerized and/or cross-linked to form a gel which absorbs or releases a liquid or vapor in response to a temperature change at the CST.

Polymers having a CST are well known in the literature. See, for example, Molyneux, *Water-Soluble Synthetic Polymers: Properties and Behavior*, CRC Press, Boca Raton, Florida (1983); Finch, C. A., ed., *Chemistry and Technology of Water-Soluble Polymers*, Plenum Press, New York (1983) at 163. A combination of hydrophobic and hydrophilic components may be selected to form a desired CST characteristic.

The majority of CST polymers exhibit phase separation or precipitation upon cooling and are referred to as including an upper critical solution temperature (UCST) characteristic. A number of polymers of interest, however, exhibit precipitation upon heating. The temperature at which precipitation occurs is referred to as the lower critical solution temperature (LCST) of the polymer.

Polymers having upper critical solution temperatures (UCST) include many diverse polymers. A few aqueous systems include polyacrylic acid, polymethacrylamide and polyvinyl alcohol. Polymers that exhibit a lower critical solution temperature (LCST) include polyethylene oxide, polyvinylalkylethers, polyvinylmethyl oxazolidone, polymethacrylic acid, substantially hydrophobic N-substituted acrylamide polymer, hydroxy alkyl celluloses as well as alkylcelluloses. See Finch, C. A., ed., *Chemistry and Technology of Water-Soluble Polymers*, Plenum Press, New York (1983) at 157.

Where the polymer gel includes an N-substituted acrylamide, N- or N,N-alkyl substituents of interest include methyl, ethyl, propyl, butyl, phenyl, pyrrolidine or piperidine groups. Cellulosic polymers of particular interest are hydroxymethyl cellulose, hydroxypropyl cellulose, hydroxypropylmethyl cellulose and copolymers thereof. As noted above, many combinations of hydrophilic and hydrophobic components may be used to create a LCST polymer that has a LCST within a desired range. For example, hydroxypropylmethyl cellulose having a LCST of about 50° C. may be modified to a LCST of about 55° C. by binding hydrocarbon side chains to the polymer. The change in LCST is in direct proportion to the amount of hydrocarbon branches attached to the polymer chain. Acrylamide may also be copolymerized with NIPAAm in a ratio of 10% to 90% respectively, and this will raise the LCST from about 31° C. to 37° C.

Some polymers may exhibit both an LCST and a UCST. Polyethylene oxide is an example of such a polymer.

As noted above, the present invention utilizes polymer gels having a suitable CST character. In a typical method for preparing such a gel, an N-alkyl-substituted acrylamide, such as N-isopropyl acrylamide monomer, is mixed in a dimethyl sulfoxide (DMSO) solution with a cross-linking agent, such as methylene bis-acrylamide. Polymerization catalysts such as benzoyl peroxide and dimethyl toluidene are stirred into the mixture to initiate and speed polymerization. The mixture is allowed to polymerize for 30–60 minutes with cooling. The resulting gel is washed to remove solvents and catalysts.

The pore structure, pore size, pore distribution and absorbing capacity of the gel produced are determined by a number of factors, such as the amount and composition of cross-linker incorporated into the gel and the solvent selected for the synthesis, as well as the concentration and composition of the monomers employed. The addition of co-monomers, as well as their hydrophobic or hydrophilic character, likewise may have a major impact upon gel pore structure as well as LCST or UCST.

Careful choice of ingredients and the synthesis parameters noted above allow production of a gel that is capable of selectively retaining or excluding molecules on the basis of size. Relatively lower levels of cross-linking agent for a given monomer will result in larger pore sizes. Where self-supporting gels are desired, however, pore size increases effectuated by means of reducing cross-linker are limited by the mechanical strength the gel must retain in order to hold together. For larger pore sizes with the same monomers, the gel may be incorporated within (another polymer or), attached to or applied as a coating on a supporting surface or base. The polymer gel coating could be attached chemically or by means of plasma discharge, ionizing radiation, UV process, ozone process or the like. The gel may be cross-linked during or after processing using a variety of means to effect the cross-linking, including incorporation of cross-linkers during the coating or incorporating process as well as the use of cross-linking compounds, ionizing radiation or UV after the system is polymerized.

The selection of cross-linking agents is one of the determining factors in achieving a desired gel pore size, which will be important for larger substrates or other reactants. The cross-linker may be hydrophobic or hydrophilic. The hydrophobic cross-linker may be any short di- or trivinyl or di- or triallyl monomer, such as methylene bis-acrylamide. A hydrophilic cross-linking agent may be, for example, a long-chain polyethylene glycol, both ends of which include double bonds for binding to the polymer backbone. Thus, the choice of cross-linker permits covalently bonding into the polymer gel hydrophobic or hydrophilic groups, which will effect the pore size and its distribution.

The concentration and composition of the initiators used in a free-radical polymerization can also influence the average polymer molecular weight and its distribution (P. F. Flory, "Principles of Polymer Chemistry," Cornell University Press, 1953). The same is true of chain transfer agents which are usually added to lower the average molecular weight. Thus, the composition and concentration of initiators and chain transfer agents may be selected to control the average molecular weight and its distribution in the CST polymer system. This in turn can provide another measure of control of pore size and its distribution in LCST hydrogels and coatings on other polymers.

The rate at which various molecules will be delivered from or absorbed into a gel also depends upon pore size and structure of the gel. Of particular interest are relatively rapid absorptions or releases on the part of the CST gel over very narrow temperature ranges. Where the solution containing the substance is physically held within a gel, there is a substantially free solute or solution component which is held as pore water. A second component of the solute or solution is bound through physico chemical interactions with the backbone of the polymer gel. When employed as a delivery tool, an LCST polymer, for example, heated above its LCST, will shrink and release the pore solute or solvent. The physico-chemically bound portion of the retained solution is released, however, over a greater length of time than the free solution. It should be noted that, as the gel collapses, only those molecules small enough to penetrate the pores will be released from the gel. Thus, the very large molecules which may be entrapped within the gel may not be able to escape as the gel collapses. This separation of molecules on the basis of size will depend very much on the average pore size within the gel as well as the pore size distribution within the gel. As discussed above, these gel factors can be controlled by careful control of the synthesis of the gel. Incorporation of relatively high levels of cross-linker, for example, broadens the temperature range as well as the time period over which the separation (absorption) or delivery (desorption) occurs. Such an extended response may be desired, depending upon the particular environment of interest.

Including a second CST polymer in the gel polymerization mixture produces a gel which has two CSTs, each reflecting the character of its backbone polymer composition. An interpenetrating network (IPN) of the two polymers is formed. Thus, water or solution evolution from a gel in a delivery process for such an IPN gel will show two distinct drops in swelling solution content as temperature is increased through the first and then the second LCST.

As noted above, the present invention allows the immobilization of a ligand within the gel in a manner such that the ligand may be exposed to and/or isolated from an environment through the gel's CST. The term "cycling", as used herein, means adjusting the temperature of the CST polymer gel through the CST range, whereby the gel becomes solvated, followed by desolvating, or vice versa, as the CST is passed.

A ligand (binding pair) immobilized within the gel may be cycled through the gel CST to imbibe solution from an environment and bind a substance of interest. Further temperature cycling will expel unbound substance/solution. The ligand bound substance may then be released from the immobilizing binding pair component by further cycling the gel in an eluting solution that breaks either the bond to the polymer gel or the binding pair bond. The substance of interest may then be expelled from the gel. The eluting solution may effect the breaking of the bonds or linkage by a change in pH, the presence of certain ions and ionic concentrations, the presence of hydrogen bonders, certain solvents, water structurers, destructurers, oxidants or reductants, reactants, affinity ligands and the like.

As noted above, a substance may be delivered to or removed from an environment by employing a ligand that is immobilized within the CST polymer gel. The immobilized ligand may be selected for its capability of specifically binding with the substance. Alternatively, the ligand selected may bind non-specifically with the substance of interest, as well as other similar substances present in the solution.

In one particular embodiment, an active ligand component may be physically or chemically immobilized or entrapped within the gel pores. The ligand may be physically entrapped by forming the gel in the presence of added ligand molecules. For example, an enzyme or an antibody may be physically trapped in the gel because they are generally large molecules. The retained molecules in such a case will be immobilized within the gel and will not leach out even though they are not chemically bound to the gel via a vinyl type of conjugation.

The ligand may also be incorporated by chemically coupling it to the CST polymer or copolymer gel backbone after it is formed or by first conjugating the ligand compound with a monomer and then copolymerizing that species with free monomer and cross-linker. Alternatively, a CST gel may be formed by copolymerizing a preactivated monomer (such as N-hydroxy succinimide acrylate (NHS- acrylate)) with the monomers of the CST polymer system, followed by coupling the ligand to the preformed polymer by contacting it with the activated backbone polymer.

In all these cases, one may utilize arms or tethers to attach the ligand to the CST polymer gel backbone. These arms or tethers may be stable or labile to the absorbed or imbibed solvent system at any particular temperature. Similar principles apply to the incorporation of chemically or biochemically active agents within the CST gels.

A biomolecule such as a drug or an antibody may be immobilized to the polymer backbone of an LCST gel by labile linkages. Such linkages might be labile to enzymes or to imbibed aqueous solvent having specific pH's. Thus one may immobilize a drug, an antibody, or other biomolecule to the backbone of this gel via such linkages, and keep the gel in a dry or shrunken state. When such a gel is immersed in a solution below its LCST, it will swell and imbibe solvent, and if the solvent has the capability of degrading the linkage, then the drug (or antibody/antigen complex) or other biomolecule will be released from the backbone of the gel, and upon subsequent warming may be released from the gel into the surrounding environment as the gel collapses above its LCST.

The ligand immobilized (physically and/or chemically) within the polymer gel may be a binding component of an affinity binding pair. Suitable affinity binding pairs include an antibody which binds with an antigen or hapten of interest. A receptor may be bound to the polymer gel that is designed to bind with a hormone, vitamin, lectin, drug, dye or lipid binding partner in solution. Other ligand binding pair components include lectin and polysaccharide or glycoprotein; DNA, RNA (single- or double-stranded) with complementary DNA, RNA or oligonucleotides or proteins or steroids; ion with chelator, ionophore, complexer; and stable-free radical with free radicals.

Suitable ligands for immobilization within the gel may also include a nonspecific binding component that is suitable for reacting with a binding partner of interest in an environment. For example, an anion or polyanion could be incorporated or immobilized within the polymer gel and bind, via ionic bonding, with a cation or polycation in the environmental solution. An anion and cation pair in the environmental solution could bind with a polyanionpolycation complex within the gel. One may immobilize a lipid or hydrophobic ligand within the polymer gel which would bind via hydrophobic bonding with a lipophile in solution. Acid/base-type interactions could be used to affect binding by immobilizing an electron donor which binds to an electron acceptor or a proton acceptor that binds with a proton donor.

Alternatively, a chemically or biochemically active reactant may be immobilized within the CST polymer gel, thereby providing a unique means of establishing a temperature-dependent control over a reaction. A key benefit of the present invention is, then, that reactions may be cycled on and off as exposure of the immobilized reactant to a reaction environment is cycled on and off in reponse to a temperature change that passes through a CST point. Such a system, for example, could include an enzyme immobilized within a CST polymer gel to catalyze a reaction with a substrate in a solution of interest.

Generally, any catalyst may be immobilized within the gel, reacting with solution co-catalysts or reaction components upon appropriate adjustment of temperature to bring the solution into contact with the gel-immobilized catalyst. Oxidizing or reducing agents may be immobilized within CST gels to react with their opposite in solution. Likewise, acids or bases may be immobilized for the control of pH sensitive reactions. A dye, latent dye or dye generator may be immobilized within the polymer gel that, in response to an environment containing an acid or base, specific ions, oxidants, reductants, dye binders, fluorescent quenchers or the like, produces an observable optical (color, fluorescence, luminescence) change or electrochemical signal change. A free radical chain transfer group could be immobilized within the gel, such that, upon exposure to a solution of interest, the retained group reacts with free radicals in the solution of interest. As a result, this reaction may terminate a different reaction or the reaction may produce reactive sites on the gel matrix for further processing.

A change in temperature at the CST involves a number of physically observable changes in a polymer gels of the present invention. For example, increasing the temperature of an LCST polymer above its LCST causes a swollen gel to shrink noticeably and become somewhat hard or brittle. These mechanical and/or dimensional polymer gel changes can be used to affect mechanical movements that serve to signal a temperature change. Conversely, a temperature change can be used to affect mechanical or dimensional changes.

Wettability of the surface of the CST polymer gel changes as its temperature changes through the gel CST. An LCST polymer gel loses wettability as the temperature is raised through the LCST. These changes are observable by means of conventional contact angle measurements. In addition, the wettability phenomenon is important for surfaces which are in contact with reactant solutions. Surfaces may be wetted or dewetted as the temperature is varied above the CST for a desired effect. For instance, the wetting or dewetting could be used as a signal to transfer heat into or out of the system, or could be used to eliminate fouling components from a surface.

The gels of the present invention also change optical characteristics at the CST. For example, increasing a gel temperature above its LCST causes the gel to become opaque. If an enzyme is immobilized within a gel and is included in a membrane system that is viewed optically, a temperature increase to an undesirable level could be detected by a change in the optical transmission of the gel membrane. This change can be used to generate a signal providing feedback to a coolant system that turns on and off in response thereto.

The CST polymer gel materials may also be employed in a variety of forms. For example, the materials may be utilized as films or membranes, tubes, hollow fibers, solid fibers, fabrics (woven, knit or non-woven), molded objects, solid particles, capsules, polymeric micelles or liposome-like structures. Likewise, they may be applied as coatings on solid surfaces or in the pores of porous solids, as solutions, particulate suspensions, etc. Coatings may be applied to polymers, metals, ceramics, glasses, carbons, and the like.

The cross-linked CST gels may be used for antigen binding, toxin removal, chemical assays, immunoassays, product recovery, substance delivery (e.g., dyes, pesticides, drugs, etc.), and drug delivery as well as other uses which will be apparent to one skilled in the art. If there is heat evolved or absorbed upon (a) reaction with an immobilized reactant, or (b) binding of the solution component with an immobilized reactant to the gel, and if the change in temperature caused by the heat absorption or release is sufficient to cause a temperature change through the CST, including swelling or shrinkage of the gel, the gel may then function as a microcalorimeter, or a temperature-sensitive switch. The color, size and hardness changes accompanying swelling or shrinkage may also be used to initiate an optical or mechanical switch or similar type of sensor.

In a particular system of interest, immobilization of a catalyst, such as an enzyme, in an LCST polymer gel demonstrates one advantage provided by the methods described herein. At a temperature below the LCST, the immobilized enzyme is active and effective. Increasing the temperature above the LCST shrinks the gel and inactivates the enzyme by shutting off accessibility of the reactants in the solution to the catalyst. The control function may be reversible or irreversible with respect to the activity of the immobilized catalyst enzyme, depending upon the composition of the gel. "Reversibility" means that the temperature may be cycled through the LCST with recovery of catalytic activity, i.e., the enzyme is not denatured in the temperature cycling process.

Additional systems which could be immobilized within CST polymer gels include antibodies that can catalyze chemical reactions (Pollack et al., *Science* 234: 1570–1573, 1986; Tramontano et al., *Science* 234: 1566–1570, 1986, herein incorporated by reference) and the larger biologic aggregates such as organelles and whole cells themselves. Living cells contain many enzymes and can be immobilized within LCST polymer gels such that when the temperature is warmed above the LCST, the polymer gel will shrink and squeeze out the fluid within the pores. This aqueous solution could contain the product secreted from the cells, and then would potentially enhance the recovery of that product by this rapid delivery process. Additionally, when the gel is reswollen below the LCST, this would enhance the rate of mass transfer of nutrients, enzyme substrates and other reactants, and oxygen to the cell, which it requires in order to synthesize and secrete the product of interest. Thus, a temperature cycling in such an immobilized cell system could provide both enhanced yields and enhanced rates of production of specific biological products of enzymatic processes within living cells.

The following examples are offered by way of illustration and not by way of limitation.

EXAMPLE I

A Method of Making a Thermally Reversible Gel of Poly-N-Isopropyl Acrylamide (NIPAAm)

A solution of N-isopropyl acrylamide monomer in dimethyl sulfoxide (DMSO) was prepared at various monomer concentrations. Methylene bis-acrylamide (MBAAm) was added as a cross-linker to the solution at various cross-linker ratios of MBAAm/NIPAAm. Benzoyl peroxide (BP) was added at a constant ratio of 0.001 mole BP/mole NIPAAm. The solutions were sparged with $N_2$ and kept over $N_2$ at room temperature. Then N,N dimethyl toluidene (NNDMT), a co-catalyst with BP, was added dropwise with stirring until the ratio of NNDMT/BP = 1 was reached. The solutions were each then poured quickly between glass plates spaced 0.75 mm apart and sealed at the edges. The plates were immersed in cool water and polymerization allowed to proceed 30–60 minutes. The plates were separated, the gels removed and washed to remove DMSO. Samples were cut from each gel and placed in deionized distilled water at 21° C. (or 40° C.). Solvent or water content of the gel was determined by first removing the gel sample from the solution, patting with dried filter paper and weighing. The films were dried in a dessicator to a constant weight and the water content was calculated. The table shows typical results and suggests that levels of both MBAAm cross-linker and NIPAAm have an important influence on swelling and deswelling rates. In addition, it was observed that as the films deswelled at 40° C., they shrank rapidly and became opaque and hard compared to their soft, transparent state at 21° C.

TABLE

EXAMPLE 1

| NIPAAm Percent | Cross-Linker Moles/Moles | Approximate Time to Achieve 80% Water Content on Swelling | Approximate Time to Achieve 40% Water Content on Desorbing |
|---|---|---|---|
| 35 | 0.0070 | 50 minutes | 98 minutes |
| 55 | 0.0070 | 20 minutes | 60 minutes |
| 50 | 0.0075 | 75 minutes | 60 minutes |
| 50 | 0.0150 | 28 minutes | 55 minutes |

EXAMPLE II

Size Separation

The process of making NIPAAm gels, as described in Example I, was repeated, except one group of polymer gels was synthesized in water while another group was synthesized in DMSO.

Swollen 1 mm circles of gel films were removed from deionized distilled water where they had been stored at room temperature for several days. The gels were then heated to 50° C. in buffer for 3 minutes, causing deswelling or desolvating of the gels. The deswelled films were placed in 10 ml of a 1.0 mg/ml solution of myoglobin, having a molecular weight of 17,800, and a like amount of vitamin $B_{12}$, having a molecular weight of 1,350. The samples were incubated at 4° C. overnight. The films were then removed from the original solution, quickly rinsed in room temperature buffer and then deswelled in 10 ml of warm buffer at 50° C. for 4 minutes.

Figure 2:
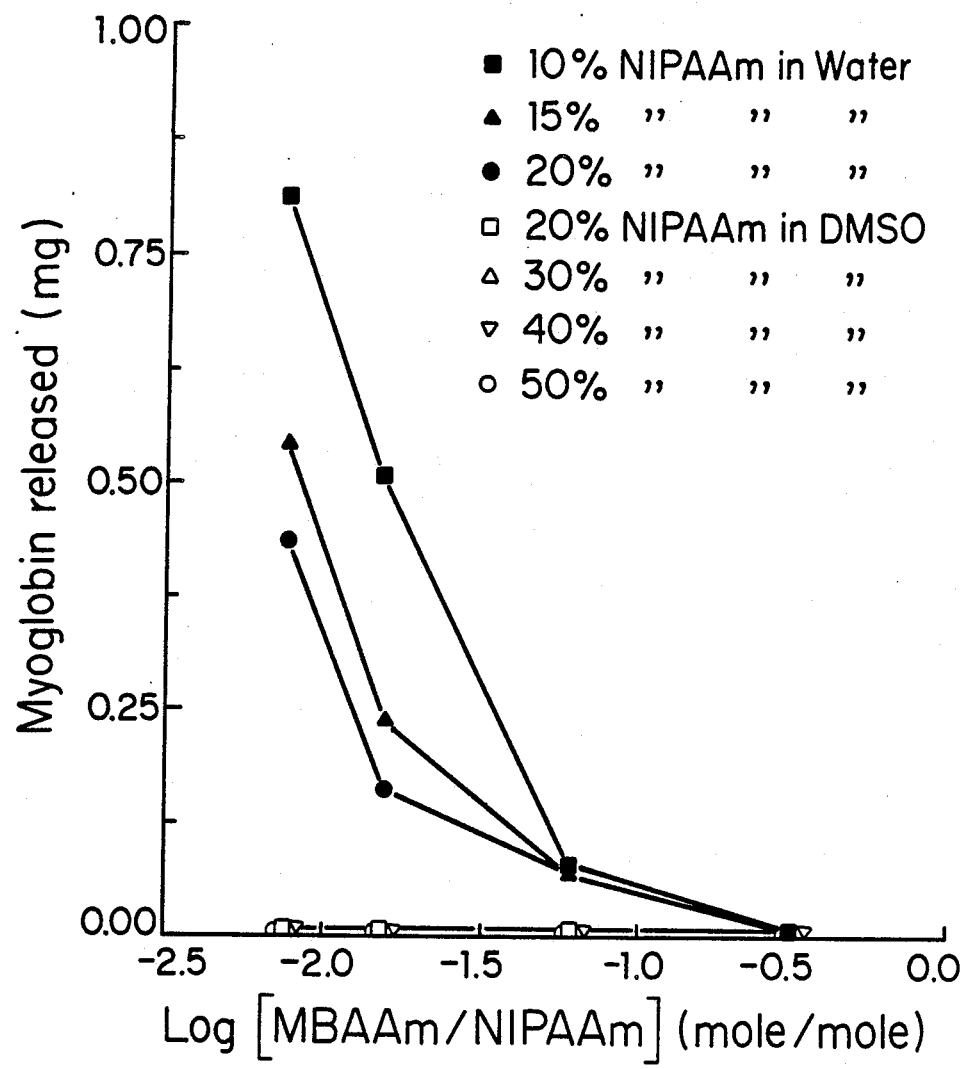
FIG. 2 depicts myoglobin delivery as a function of cross-linker/monomer ratio for various NIPAAm polymer gels synthesized by the indicated solution, monomer and solvent compositions.

Concentrations of the myoglobin and vitamin $B_{12}$ released were determined by absorption at 280 nm and 360 nm, respectively. FIGS. 1 and 2 report the weight ratio of myoglobin or vitamin $B_{12}$ to buffer released, reported as a function of cross-linking agent/monomer ratio densities. Comparing polymer gels made with 20% NIPAAm monomer in water with the 20% NIPAAm polymerized in DMSO shows that the water-synthesized 20% NIPAAm polymer absorbed and delivered myoglobin while the DMSO-synthesized 20% NIPAAm gel did not. Referring to FIG. 1, vitamin $B_{12}$/buffer release as a function of cross-linker to monomer ratio is reported. FIG. 1 reports that both the 20% NIPAAm gels, whether polymerized in DSMO or in water, absorbed and delivered vitamin $B_{12}$.

The comparison of the FIGS. 1 and 2 curves for 20% NIPAAm demonstrates that LCST hydrogels are capable of distinguishing, with respect to absorption and delivery, on the basis of molecular size. The example demonstrates that selection of important synthesis factors, such as cross-linker to monomer ratio and synthesis solution composition, may be used to affect the removal or delivery of molecules or substances from or to the environment.

Figure 3:
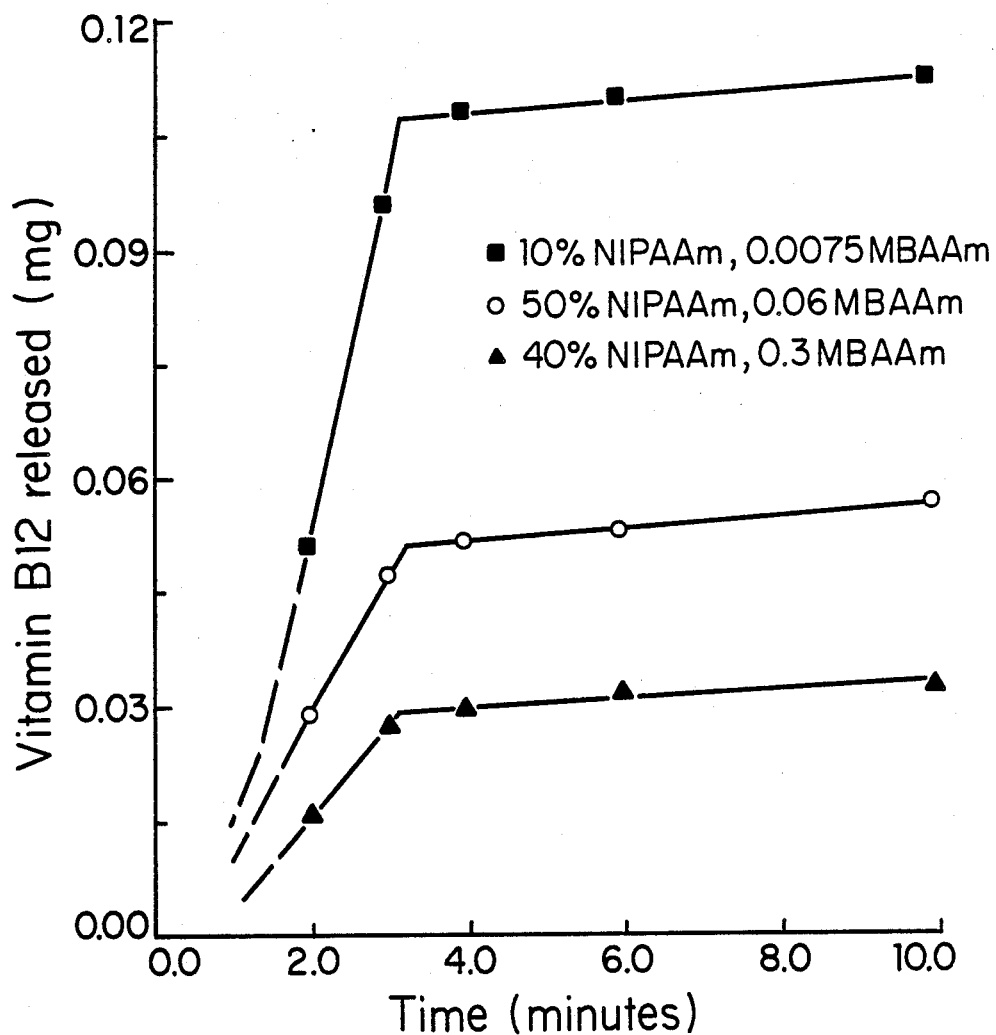
FIG. 3 illustrates the delivery of vitamin $B_{12}$ as a function of time for three different polyNIPAAm gels.

Referring to FIG. 3, the ratio of vitamin $B_{12}$ to buffer released on heating polyNIPAAm gels from 4° C. to 50° C. as a function of time is reported. Release kinetics of vitamin $B_{12}$ from various gels show two regions over time. The first region, occurring within the first five minutes of the temperature change, is a relatively sudden release of the solution nearest the surface of the gel and retained within its pores. The region thereafter shows a much slower diffusion rate out of the gel after the initial stage shrinkage is complete. This diffusion region shows the slower release of solution entrapped by molecular entanglements and/or bound by attracting forces within the polymer matrix. The ratio of diffusion delivery to initial pore collapsed volume delivery may be controlled by gel composition and solution composition used in the gel formation, as demonstrated by the family of curves reported.

EXAMPLE III

NIPAAm Gels Copolymerized with Methacrylic Acid

Five ml portions of 20% NIPAAm solution and deionized water were combined with solutions of methacrylic acid (MAAc) to yield MAAc contents ranging between 0–5%, in 1% increments. Thus, 0, 10, 20, 30 and 50 ml portions of 10% methacrylic acid were combined with the NIPAAm solutions. 0.0073 mole of MBAAm per mole of NIPAAm was added as a cross-linker. The resulting solution was degassed, followed by addition of 10 microliters of N,N,N',N',tetramethylethylenediamine (TEMED) and 10 microliters of 10% ammonium persulfate as a redox initiator system. The resulting solution was poured between two glass plates spaced 0.75 mm apart and polymerization allowed to proceed for 2 hours at 20° C. The water contents of the resulting polymers as a function of temperature were determined. In these measurements, the polymer gel was first allowed to equilibrate in a buffer or deionized water at various temperatures for 24 hours. The gel was then removed for weighing to obtain a wet weight. The gel was then dried to constant weight and percent water content was calculated as 100 (wet weight−dry weight)/(wet weight).

Figure 4:
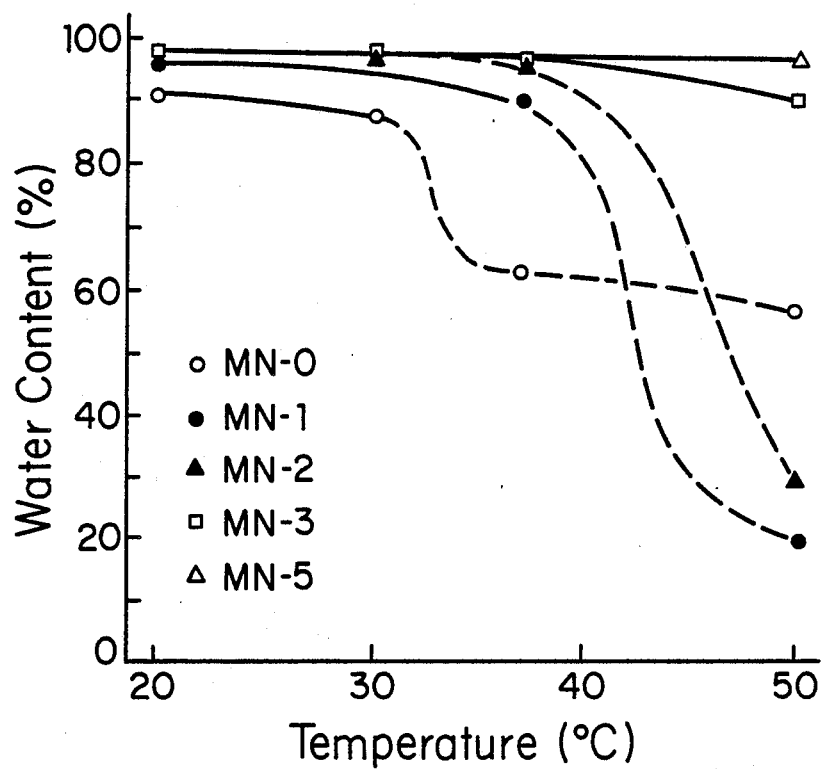
FIG. 4 demonstrates the impact on water contents vs. temperature of copolymerizing methacrylic acid with NIPAAm to form LCST polymer gels.

FIG. 4 demonstrates the effect of temperature on water content of LCST gels including various percentages of methacrylic acid.

The data show that increasing methacrylic acid content shifts the LCST to higher temperatures. The MAAc content also has a significant influence on water content at higher temperatures. As shown in FIG. 4, some gels have passed through their LCST, while others have not reached their LCST. It is possible that at high enough comonomer contents the gel will not exhibit an LCST up to 100° C. in water.

EXAMPLE IV

Methylene Blue Absorption and Delivery as a Function of Methacrylic Acid Content of NIPAAm Polymer Gels Gel polymer samples were made in accordance with Example III above, in which 0–5% methacrylic acid, in separate samples at 1% increments, was copolymerized with the poly-NIPAAm polymer. Methylene blue was absorbed into those samples in order to determine delivery capabilities as a function of amount of methacrylic acid incorporated within the gel.

The dried gels were equilibrated in a dye solution of 1% methylene blue dissolved in a 50/50 methyl alcohol and a 0.1M Tris buffer (pH 8.61) solvent for 24 hours at room temperature. The polymer gel is dipped in a buffer at pH 7.4 at 20° C. for 1–2 seconds to wash off excess solution on the surface. The gel is then placed in a buffer to release the methylene blue at temperatures of 20°, 30°, 35°, 40° and 50° C. The amount of methylene blue released into the solution was determined using a UV-visible spectrophotometer. The following table reports the methylene blue initially absorbed into the gels.

TABLE

EXAMPLE IV

| % METHACRYLIC ACID | % METHYLENE BLUE* ABSORBED INTO THE GEL |
|---|---|
| 0 | 1.5 |
| 1 | 4.1 |
| 2 | 4.9 |
| 3 | 8.3 |
| 5 | 11.5 |

*(Weight % of Dry Gel)

Figure 5A:
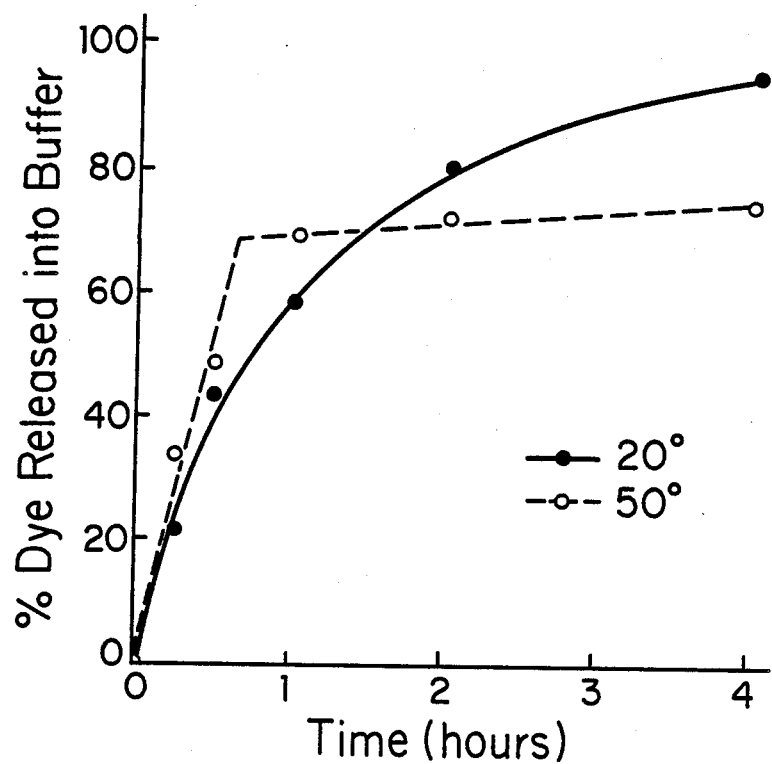
FIGS. 5 (a-c) depict the release of methylene blue at 20° C. and 50° C. as a function of time for NIPAAm polymer gels copolymerized with up to 5% methacrylic acid.
Figure 5B:
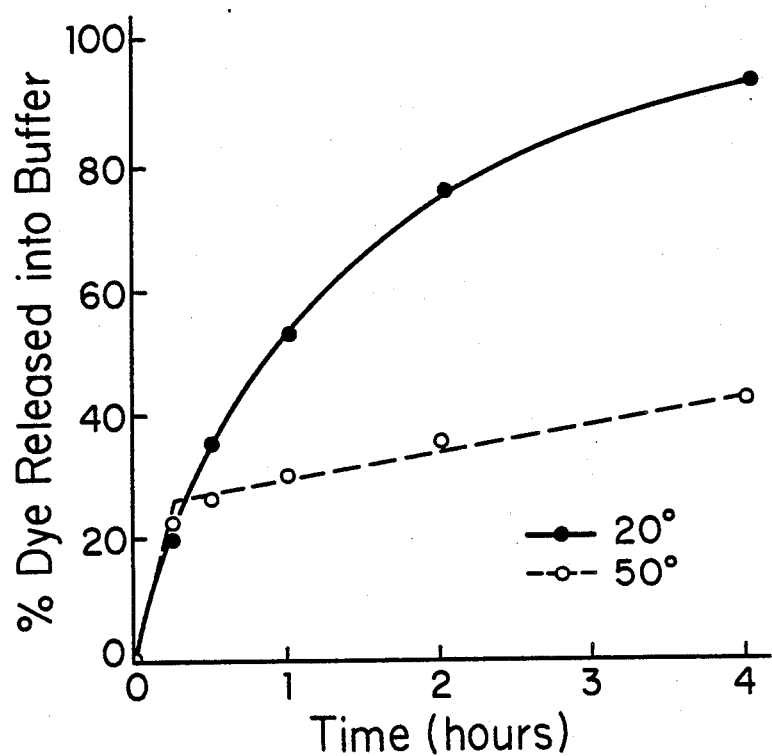
Figure 5C:
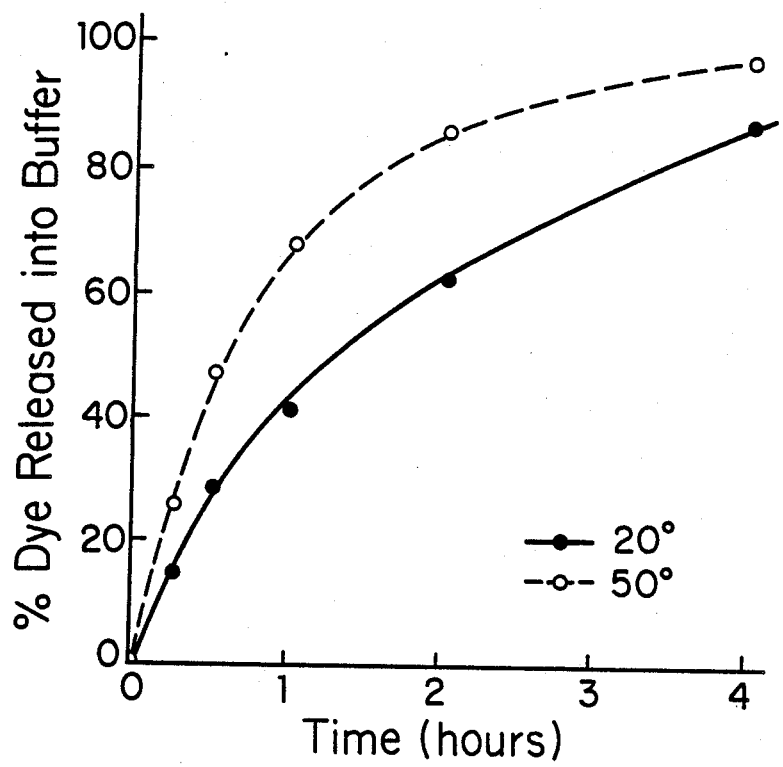

FIGS. 5 (a–c) show dye release into the buffer as a function of time for various percentages of methacrylic acid content of the polymer at 20° and 50° C. The data demonstrates release of methylene blue that is bound to the polymer gel of the invention by action of its affinity to the negative charge on the methacrylic acid carboxyl group ($-COO^-$) since the methylene blue is positively charged.

The release over time is at two significantly different rates, as the temperature is increased above the LCST. There is an initial rapid release as the dye which is most accessible to the pore water releases. Thereafter, there is a gradual release as the bound portion of the methylene blue diffuses from the polymer gel into the buffer solution. The percent of methylene blue released at 50° C. for the 1%-methacrylic acid gel (MN-1) is less than that for the gel including no methacrylic acid (MN-0), since the methylene blue is ionically bound by its affinity to the methacrylic acid groups contained within the NIPAAm-methacrylic acid copolymer gel. This is an example of nonspecific binding of a ligand (the COO- group) and its binding partner (methylene blue).

The release curves at 20° C. for the MN-0 (0% MAAc, FIG. 5a) and MN-1 (0% MAAc, FIG. 5b) and at 20° C. and 50° C. for the MN-5 (5% MAAc, FIG. 5c) gels are smooth and show typical first order release rates since these gels are swollen and below their LCSTs.

Figure 6:
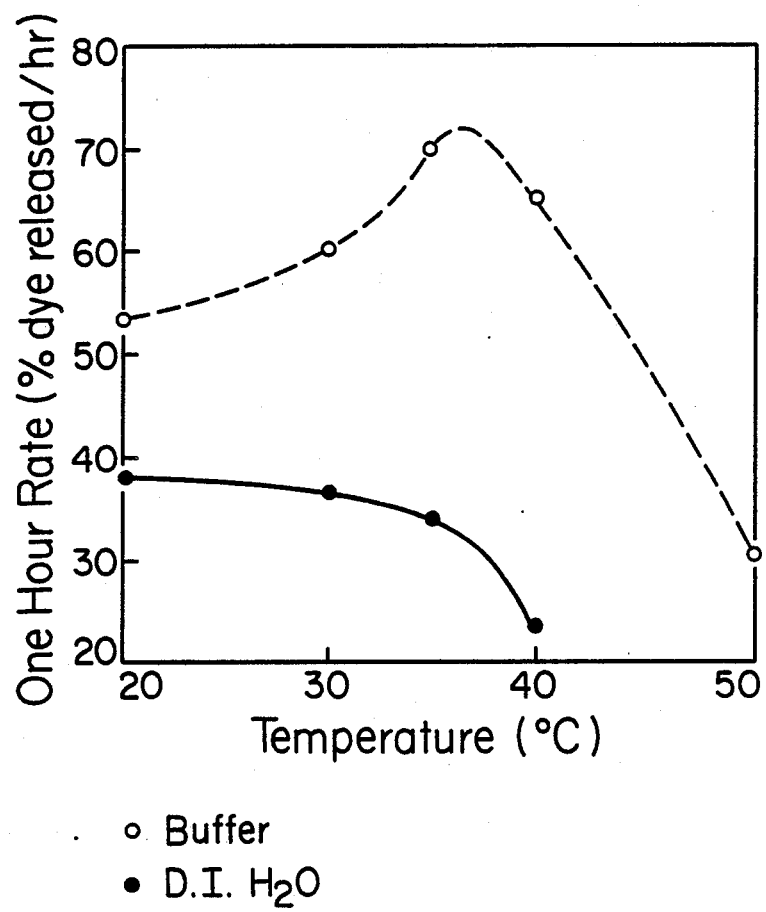
FIG. 6 depicts the release rate, as a function of temperature, of methylene blue from a cross-linked polyNIPAAm gel containing 1% methacrylic acid in a buffer solution and in distilled water.
Figure 7:
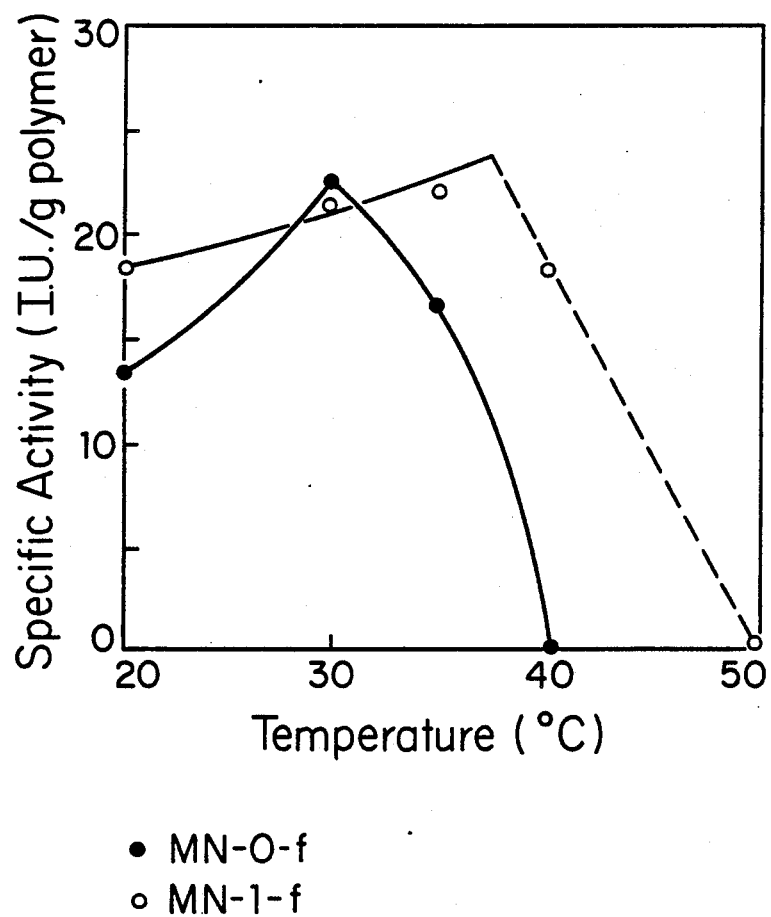
FIG. 7 illustrates the temperature dependence of specific activity after a first test cycle between 20° C. and 50° C. for an enzyme which is physically held within the LCST polymer gel of the invention, wherein MN-O refers to a polyNIPAAm gel and MN-1 is a polyNIPAAm gel also including 1% MAAc.
Figure 8:
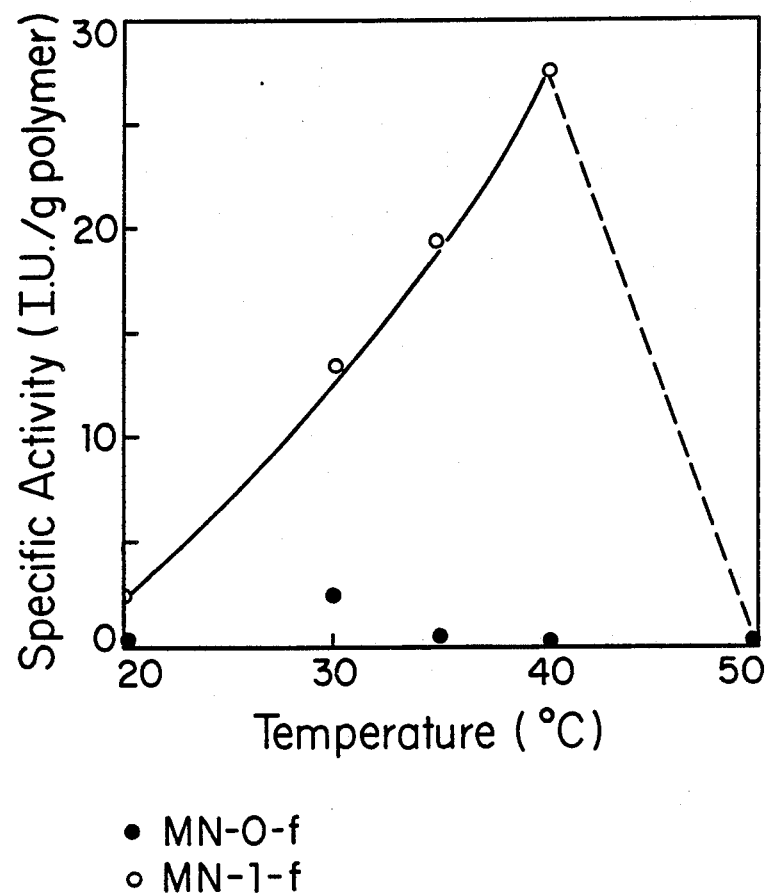
FIG. 8 depicts the specific activity of the enzyme for the gels of FIG. 7 for the third temperature cycle between 20° C. and 50° C.
Figure 9:
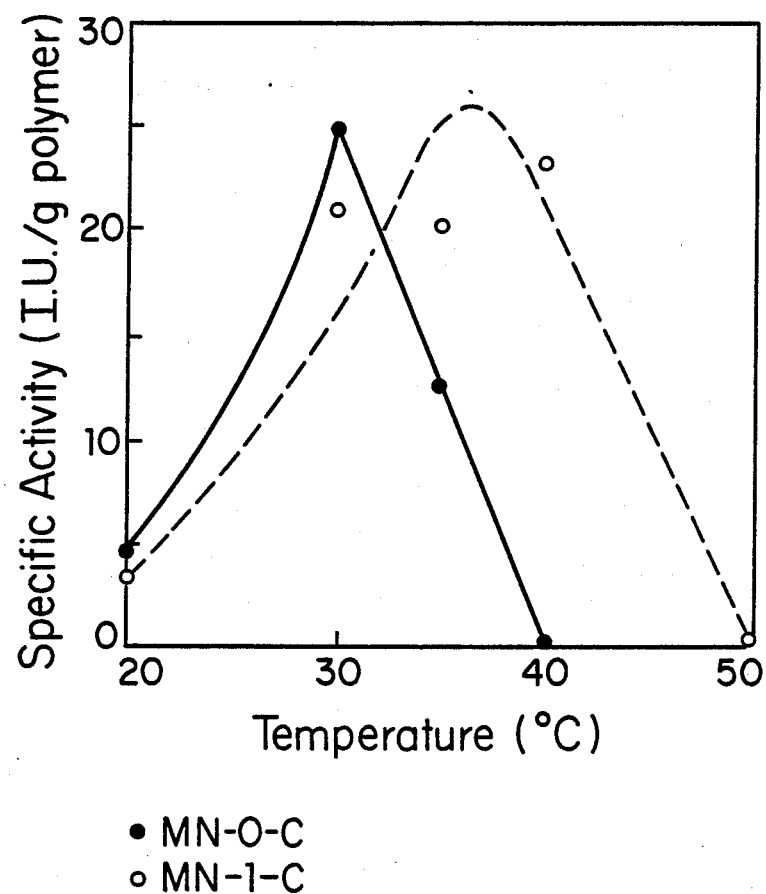
FIG. 9 illustrates the temperature dependence of specific activity of an enzyme conjugated to an LCST polymer gel of the invention after a first test cycle between 20° C. and 50° C.
Figure 10:
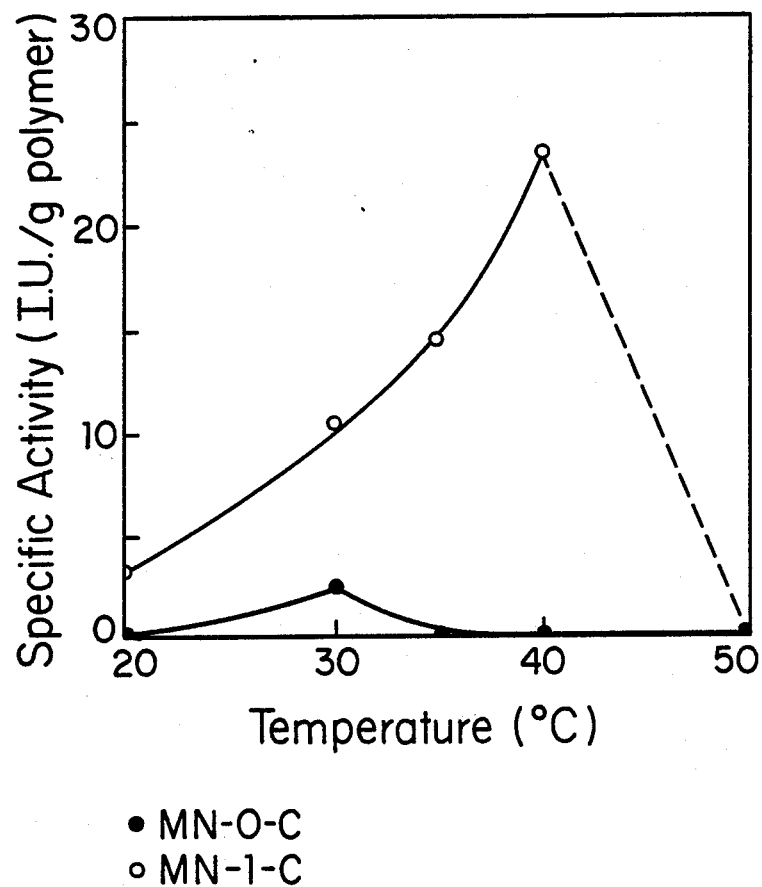
FIG. 10 depicts the remaining specific activity of an enzyme for the third temperature cycle between 20° C. and 50° C.

A comparison of the release rates of methylene blue into aqueous buffer or distilled water from NIPAAm polymer gels including 1% methacrylic acid was conducted. The results, as depicted in FIG. 6, show that including buffer salts in the surrounding solution made it easier to deliver methylene blue on heating above the LCST. This occurs because the salts break the negative/positive ionic bond between the negatively charged methacrylic acid component of the gel and the positively charged methylene blue. Thus, the buffer is acting as an eluting solvent. This action is important in both release and recovery of many binding partner solution components. Other systems of interest include, for example, assaying antigen in an immunoassay or recovering a product such as a peptide vaccine (which acts as an antigen to an immobilized antibody), when using these gels for bioseparations. The first binding partner, e.g., antibody, may be immobilized within the gel by including it in the polymerization solution as the free binding partner, or as the monomer conjugated binding partner. The immobilized binding partner may be any of the specific or nonspecific binding partners, as listed above.

EXAMPLE V

Asparaginase Enzyme Activity After Immobilization Within NIPAAm and NIPAAm-Methacrylic Acid Polymer Gels In this procedure, 5 ml of 20% NIPAAm solution in 0.1M Tris buffer (pH 8.6) were mixed with various percentages of methacrylic acid, as noted above. The solution was combined with a MBAAm cross-linker in the ratio of one mole of cross-linker per 750 moles NIPAAm. To this solution, an oxidizing redox catalyst component, comprising 10 microliters of 10% ammonium persulfate solution in distilled deionized water, was added. The mixture was degassed under vacuum and blanketed with nitrogen. 0.5 ml of asparaginase enzyme solution in 0.1M Tris buffer was added to the mixture. An enzyme concentration of 3.32 mg/ml was added where the enzyme was monomer conjugated and bound to the polymer gel backbone after polymerization. A concentration of 4.0 mg/ml was added to the polymer gel where the enzyme was not monomer conjugated but still ended up immobilized in the gel. Ten ml of TEMED reducing catalyst component was next added to the mixture. The mixture was then poured between two glass plates, as noted above, and polymerization allowed to proceed for 2 hours at 20° C. The resulting gels were washed in a 0.1M Tris buffer, Triton-X-100 and buffer solution, and the resulting washed gel stored in 0.1M Tris buffer at 4° C.

Samples of the gel were taken to determine the asparaginase enzyme specific activity after the gels had been cycled through three 20° C. to 50° C. temperature sequences.

For each specific activity determination, the gel sample was brought to equilibrium in 5 ml of 0.1M Tris buffer at 20° C. for 2 hours. The gel was then contacted with 0.02M asparagine solution in 0.05M Tris buffer for 10 minutes. The gel was then removed and a standard specific activity measurement conducted in the residual solution. In this test, the reactant solution, 0.5 ml, was mixed with 3.5 ml of deionized distilled water and 0.5 ml of Nessler reagent. Exactly one minute after adding the Nessler solution, absorbance at 420 nm was measured. The reading was converted to specific activity by comparison with a predetermined calibration curve. Tests were run at 20°, 30°, 35°, 40°, 50° C. Tests were run both for samples in which the enzyme was conjugated to the polymer and for samples where the free enzyme was immobilized in the gel. FIGS. 7–10 report the temperature dependence of specific activity for NIPAAm polymer gels that include no or 1% methacrylic acid component as well as conjugated or free enzyme immobilized within the polymer gel. Each gel sample was cycled through three 20° C. to 50° C. temperature cycles.

The data presented in FIGS. 7–10 show that the immobilized enzyme activity may be "turned off" by heating the polymer gel above its LCST, whether the enzyme is incorporated as free enzyme in the gel or as a monomer-conjugated enzyme bound to the polymer gel during preparation of the gel. The curves show that the presence of 1% methacrylic acid shifts the LCST and thus the "turn off" temperature. Further, the data demonstrate that the "turn off" mechanism is reversible, i.e., that the enzyme retains activity during a number of temperature cycles. The gels demonstrate that such reversibility is possible for some gels, such as NIPAAm containing 1% methacrylic acid, while not in others, such as NIPAAm containing no methacrylic acid. It appears that the enzyme may be denatured when the NIPAAm gel is cycled to 50° C., but remains active when the gel includes a methacrylic acid component, possible due to the higher water content of the methacrylic acid-containing gel and/or to the local pH within the gel. The temperature combined with the composition of the gel may act together to denature the enzyme.

Figure 11:
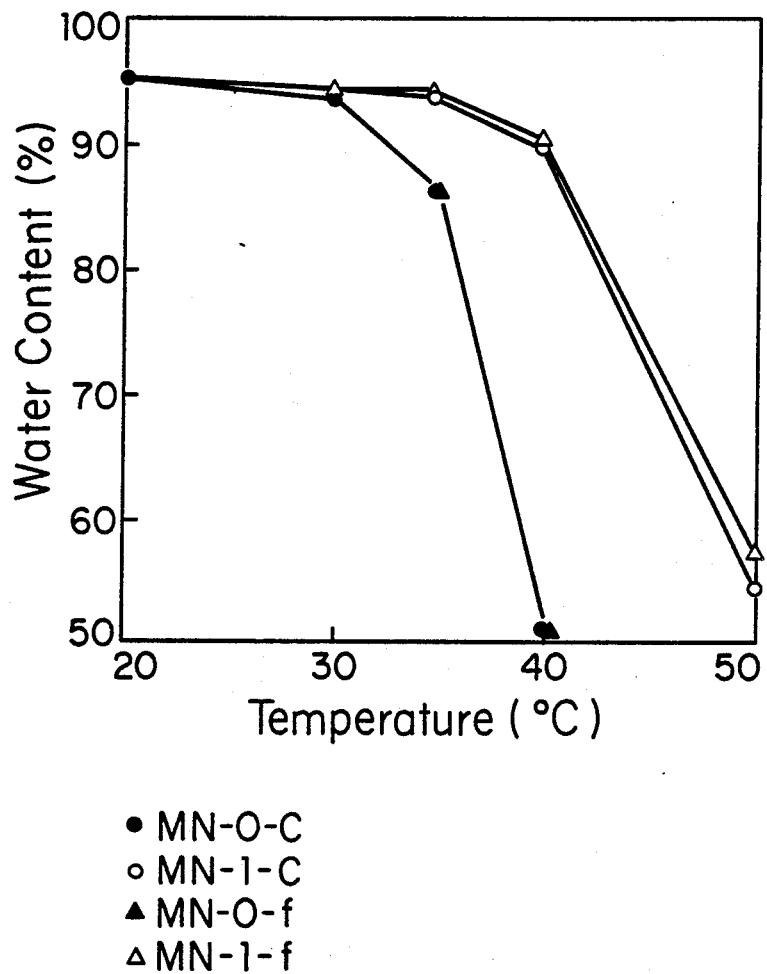
FIG. 11 depicts the temperature dependence of poly (NIPAAm) and poly (NIPAAm-MAAc) gels of the invention containing immobilized asparaginase, wherein "C" indicates enzyme covalently bonded into the gel, while "f" refers to free enzyme immobilized physically within the gel.

FIG. 11 shows the water content of polymer gels that include asparaginase, immobilized therein. These data show that the presence of enzyme in gels does not effect the water content versus temperature curves in a buffer. The enzyme may be incorporated as free enzyme or be bound onto the backbone by its monomer conjugation during gel formation. A major and controlling factor demonstrated by these data is the impact of the monomer, in this example, methacrylic acid, and its concentration.

EXAMPLE VI

Asparaginase Enzyme Activity After Immobilization Within NIPAAm and AAm Polymer Gels N-succinimidyl methacrylate (NSMA) dissolved in dimethylformamide was combined with a solution of asparaginase in 0.1M Tris buffer, pH 8.6, for a total monomer:enzyme ratio of 91.7:1. This mixture was allowed to react at room temperature for 3 hours and was terminated by addition to a Sephadex PD-10 column equilibrated with Tris buffer. The conjugated protein was eluted off the column with aliquots of Tris buffer. Collected fractions were analyzed for absorbance at 278 nm, and the more concentrated fractions were pooled for use in immobilization reactions.

Solutions of NIPAAm and AAm with a concentration of 1.75M were mixed to make NIPAAm:AAm molar ratios of 100:0 (referred to as NA-100), 95:5 (NA-95), 90:10 (NA-90), and 85:15 (NA-85) (see table below). These solutions contained MBAAm at a 1:750 molar ratio of monomer:cross-linker, and for enzyme immobilization reactions, conjugated asparaginase was added to the monomer solutions for a final asparaginase:monomer molar ratio of $1.48 \times 10^{-6}$:1. Ten ul of 10% ammonium persulfate solution was then added, and the solutions were degassed via water aspirator unitil no bubbles appeared. After addition of 10 ul of TEMED with mixing, the solutions were immediately poured between glass plates separated by 1.5 mm spacers. Polymerization was carried out at room temperature for at least one hour. The gels were then taken out of the mold and rinsed with deionized water if no enzyme was used; if enzyme was immobilized in the gel, it was washed with 1% Triton X-100 in DIW three times, then rinsed with deionized water and 0.1M Tris buffer (pH 8.6). The washed gels were cut into small discs and stored at 4° C. until tested. These gels were also cured by irradiation using a $^{60}$Co source. In this case, the redox catalyst initiator system is not needed.

TABLE
EXAMPLE VI

| Sample Code | Relative Amount (%) | |
|---|---|---|
| | NIPAAm | AAm |
| NA-100 | 100 | 0 |
| NA-95 | 95 | 5 |
| NA-90 | 90 | 10 |
| NA-85 | 85 | 15 |

Figure 12:
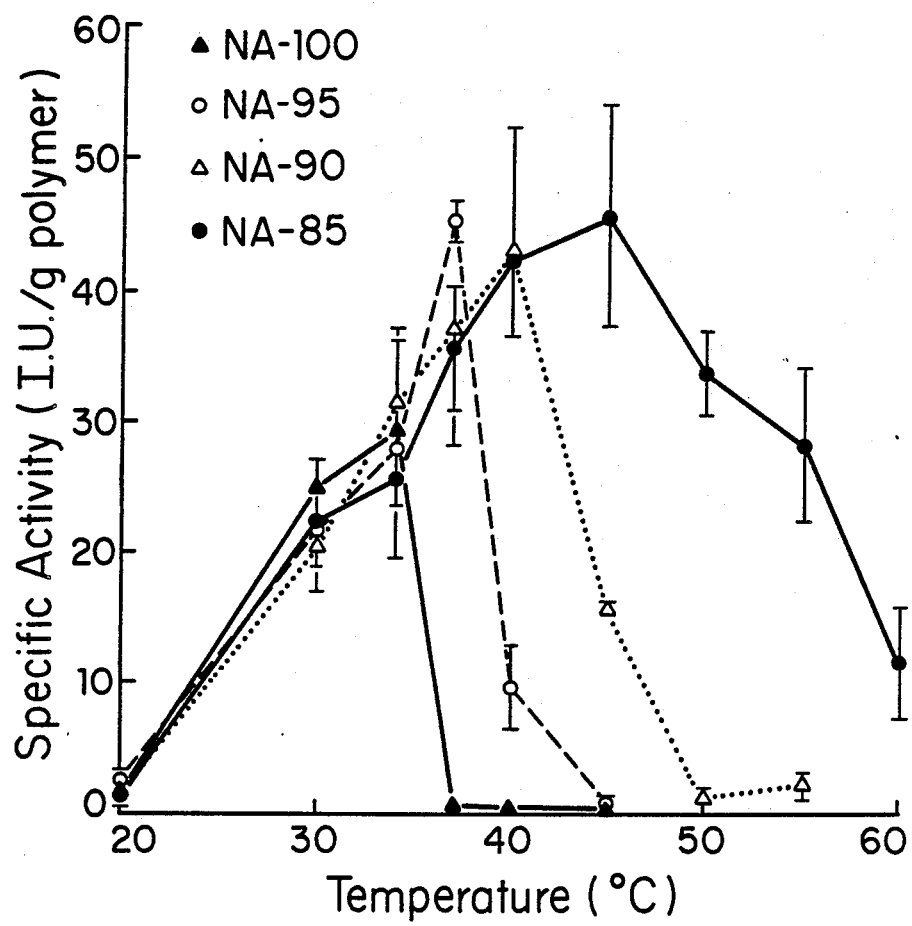
FIG. 12 illustrates the temperature dependence between 20° C. and 60° C. of specific activity of an enzyme conjugated to poly (NIPAAm) and poly (NIPAAm-AAm) gels.

Enzyme activity was measured at varied temperatures between 20° and 60°. For these measurements, the gels were first removed from storage at 4° C. and equilibrated at room temperature for 1 hour. The gels were reacted for 10 minutes at room temperature, equilibrated at 30° C. for 15 minutes, then reacted for 10 minutes in asparagine solution at 30° C. This pattern of equilibration for 15 minutes, then reaction for 10 minutes was repeated for each temperature studied. The specific enzyme activities of the gels are shown as a function of increasing temperature in FIG. 12. It can be seen that the enzyme activities parallel the water contents of the gels. Thus, the activity of the immobilized catalyst (enzyme) may be "shut off" by raising the temperature. Collapse of the gel will both retard or eliminate diffusion of reactants (substrate) into the gel as well as change the microenvironment of the enzyme.

Figure 13:
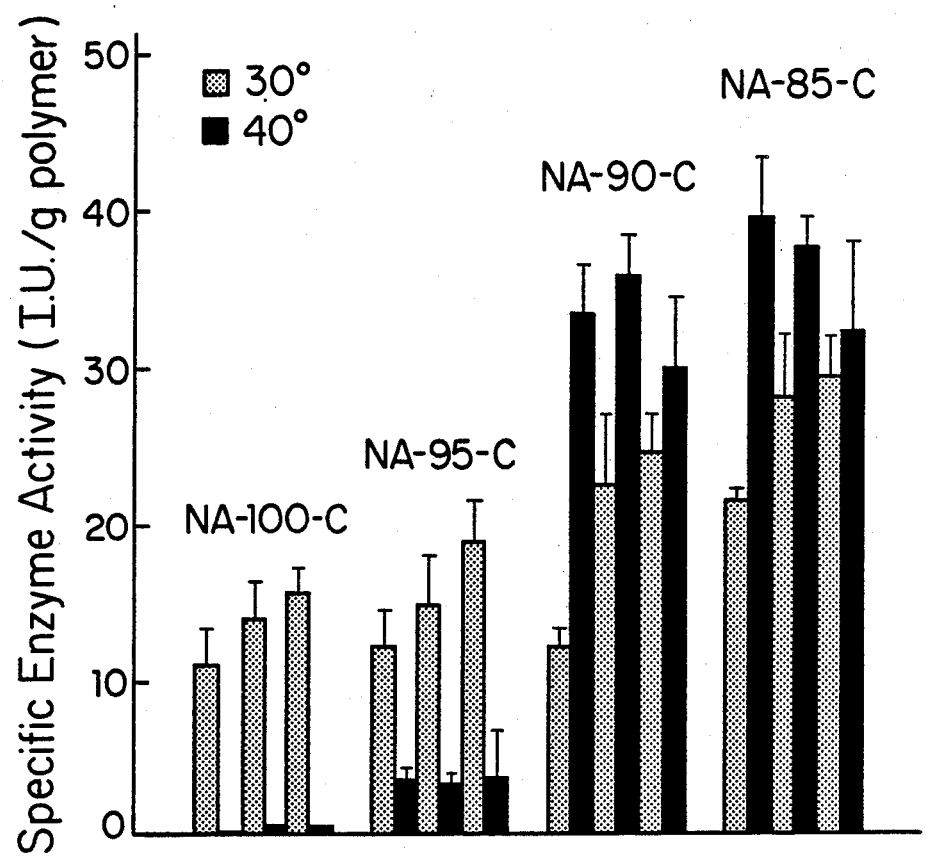
FIG. 13 demonstrates the reversibility of enzyme activity in the poly (NIPAAm) and poly (NIPAAm-AAm) gels by cycling them between 30° C. and 40° C.

If the catalytic gel is to be useful for such reaction control, it must act reversibly. The specific enzyme activities of the gels were also studied by cycling them between 30° C. and 40° C. The results are shown in FIG. 13. It is evident that the enzyme activity is reversible in all of these gels. In addition, the dramatic drop in gel enzyme activity in going from 30° to 40° for the NA-100 and NA-95 gels is in sharp contrast to the NA-90 and NA-85 gels, which show a rise in activity for the same temperature changes. This is expected because the last two gels are above their LCSTs at that temperature.

EXAMPLE VII

Use of Polymer Gel in Drug Delivery System Displaying Zero-Order Release

A 20% (w/v) solution of recrystallized NIPAAm in deionized water containing methylene-bis-acrylamide (MBAAm) at a 1:750 molar ratio of MBAAm to the monomer was polymerized between glass plates separated by 1.5 mm spacers. Ammonium persulphate (APS) and tetramethylethylenediamine (TEMED) were used as a redox initiator system. After polymerization, the gel was washed, rinsed, and cut into discs which were subsequently soaked in 2% solutions of methylene blue (MB) in methanol at room temperature. After equilibration, the gel discs were taken out of the MB solution, blotted, and dried in vacuum at room temperature. MB release was carried out at different temperatures in deionized water (DIW) on a shaker. This solution was replaced with fresh DIW after the first, and again after the fourth hour, and thereafter every 24 hours.

The release rate of MB was quite constant at both 37° C. and 50° C. The rate at 37° C. was higher than that at 50° C., the former 14.2 ug/day and the latter 8.8 ug/day. Normally one would expect the rate of release to increase with temperature. In this case, the diffusion constant should increase with temperature but the extent of water sorption should decrease. The difference in water sorption at 37° vs. 50° should be relatively small because the hydrogel is above its LCST at both temperatures. Nevertheless, the slightly larger water sorption at 37° may create a more open and less tortuous pore structure for the MB to diffuse through, which more than compensates for the lower diffusivity at 37°. Since the release of MB from the dry hydrogel immersed in water is a dynamic process with water diffusing in and MB diffusing out, the linear rate of release suggests that the water diffusion controls the delivery process. When swollen gels containing vitamin B12 are immersed wet into 37° or 50° water, the release kinetics show two linear regions, a fast rate followed by a slow rate. Only when the gel is initially dry was one linear release rate observed. Therefore, thermally reversible homopolymer gels, such as lightly cross-linked poly NIPAAm, can be employed for fabricating matrix drug delivery systems which display zero-order release.

EXAMPLE VIII

Grafted Surfaces for Minimizing Protein and Cell Adhesion

N-isopropyl acrylamide and its copolymers with acrylamide were radiation grafted to a silicone rubber substrate. The silicone rubber (SR) substrate material used was 20 mil Silastic film (Dow Corning 500-5). The monomers employed were NIPAAm and AAm and were used as received without further purification. Irradiations were carried out in a Cobalt −60 source with the films immersed in aqueous solutions of the monomers. Cupric nitrate was added to inhibit homopolymerization in the solution. In a few cases, nitrogen atmosphere was used, but in most of the studies an air atmosphere was present. After irradiation, each film was washed in deionized water overnight, dried in a dessicator, and weighed to permit calculation of percent grafting as $100 \times$ (weight of grafted film − original film weight ÷ original film weight). Water contents of the grafted films were measured at different temperatures after equilibration at each temperature overnight, followed by weighing the wet film, then drying and reweighing it in the dry state. The water contents are reported as $100 \times$ (wet weight of grafted film − dry weight of grafted film) ÷ (wet weight of grafted film − original weight of film).

Based upon empirical studies, the following experimental conditions were selected for radiation grafting: 100 mmol/l of $Cu(NO_3)_2$, 10% total monomer concentration (NIPAAm or AAm or mixtures), air atmosphere, and an irradiation of the films for 24 hours for a total dose of 0.68 Mrad.

Figure 14:
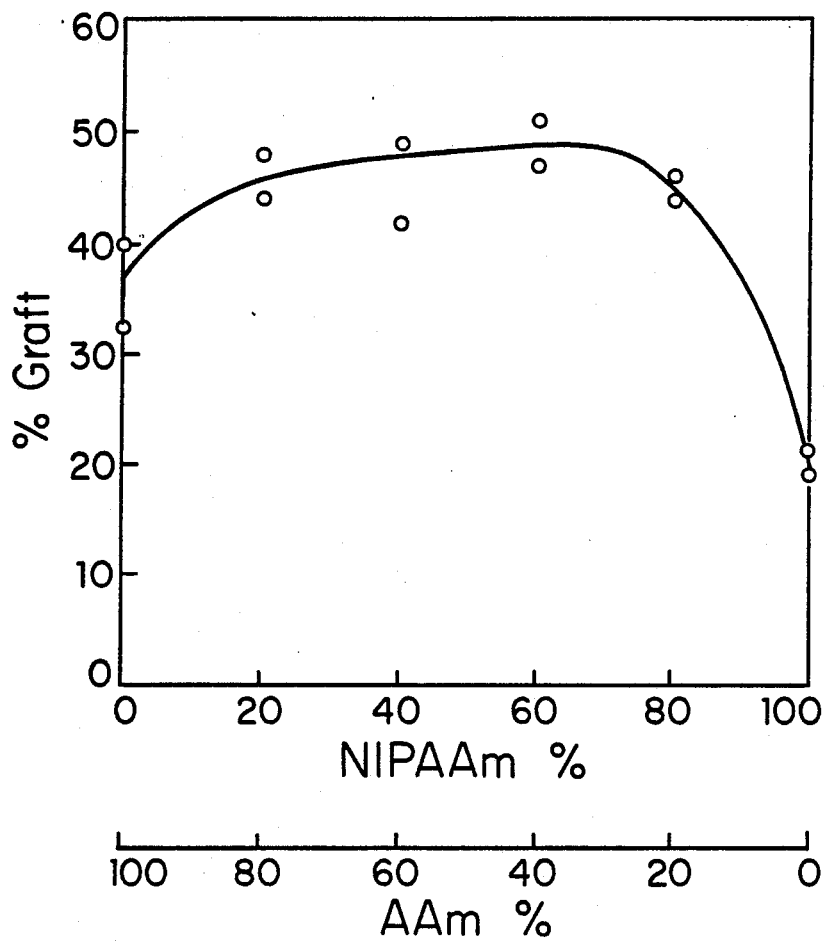
FIG. 14 depicts the percentage of homopolymers and copolymers of NIPAAm and AAm radiation grafted to a Silastic silicone rubber substrate.

Mixtures of NIPAAm and AAm were grafted to SR and the results are shown in FIG. 14. It can be seen that (10%) AAm grafts to a higher extent than (10%) NIPAAm, and also that there is a maximum in grafting at some intermediate composition. This result may be caused by a combination of effects: greater relative absorption of the NIPAAm in the SR but higher grafting reactivity of AAm, resulting in the observed maximum.

The graft water contents in the grafted copoly (NIPAAm/AAm) films was measured as a function of temperature between 5° C. and 50° C. The results are plotted in FIG. 15. The slopes of the curves indicate that the four films richest in NIPAAm (films 3-6) decrease in water content as temperature is raised, while the film grafted with pure AAm increases in water content with temperature. One film (No. 2) prepared in a 2% NIPAAm, 8% AAm solution interestingly showed no influence of temperature on water content. This is not unexpected, since poly NIPAAm precipitates out of water around 31°-33°, while poly (AAm) is the opposite and is becoming more soluble (hydrated) as temperature is raised. The 2/8 (% NIPAAm/% AAm) graft is interesting because the opposing tendencies of poly NIPAAAm to collapse and poly AAm to expand must be balanced over the temperature range studied.

Figure 15:
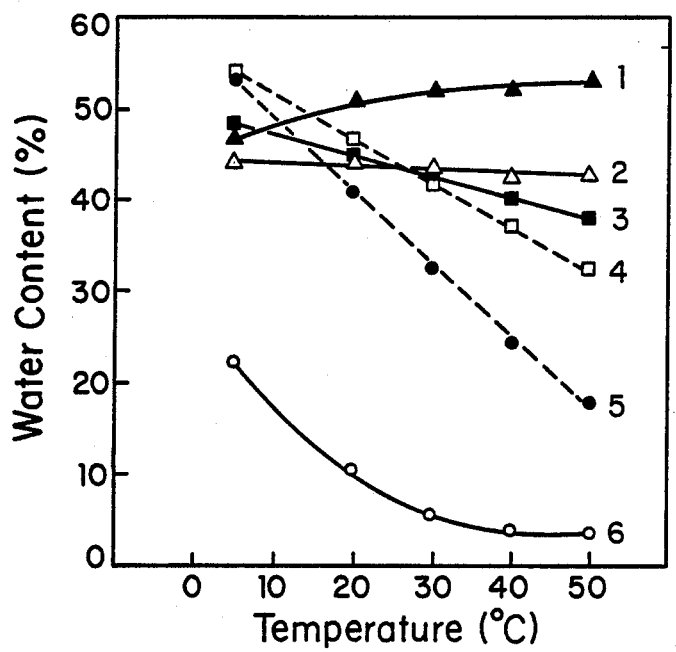
FIG. 15 presents the graft water contents in the grafted homo- and copoly (NIPAAm/AAm) films as a function of temperature between 5° C. and 50° C.

There is also in FIG. 15 an interesting crossover to be noted in the water contents of the grafted films at the lower temperatures. That is, at 5° certain intermediate compositions (films 3-5) absorb more water than the 100% AAm graft, which would have been expected to hydrate to the greatest extent. At 50%, however, the situation is different. Here, above the LCST for poly NIPAAm, even small amounts of NIPAAm in the graft copolymer reduce the water content below that of polyAAm. Apparently the driving force for poly (NIPAAm) phase separation is the dominating factor at 50° C. for all copolymer compositions. Thus, as anticipated, the crossover at lower temperatures disappears above the LCST region (31°-33°) of poly NIPAAm.

Grafting of hydrogels onto hydrophobic substrates can yield more biocompatible surfaces while retaining the desirable physical properties of the substrate material. The rationale for grafting hydrogels is based on the hypothesis that the more hydrophilic the polymer surface, the lower the interfacial energy in the aqueous biological environment and thus the lower the thermodynamic driving force for protein adsorption and cell adhesion. When polymers are radiation grafted with gradually varying mixtures of hydrophilic and hydrophobic monomers, protein adsorption and cell adhesion often exhibit a minimum at some intermediate graft copolymer composition.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for separating a desired substance from a solution, comprising:
   introducing a polymer gel, that is characterized by a critical solution temperature and having immobilized therein a binding component that is the binding partner of said desired substance, into a solution containing said desired substance; and
   adjusting the temperature of the polymer gel/solution through the polymer's critical solution temperature to allow said binding component to bind said substance and form an immobilized complex thereby immobilizing said substance from the solution.

2. The method of claim 1 including after the step of adjusting the temperature, reversing the temperature of the polymer gel back through the polymer's critical solution temperature and thereby expelling unbound solution components.

3. The method of claim 2 including after the step of reversing the temperature, transferring the polymer gel/substance from the solution.

4. The method of claim 3 including, after the step of transferring, contacting the polymer gel/substance with a solution capable of releasing said substance from said binding component, and cycling the temperature of the polymer gel/substance through the polymer's critical solution temperature, whereby said substance is released from said binding component.

5. The method of claim 4 wherein said releasing solution contains compositions selected from the group consisting of acids, bases, salts, ionic detergents, non-ionic detergents, organic solvents and chaotropic agents.

6. The method of claim 4 wherein said releasing solution contains compounds having a greater affinity to bind the desired substance or the immobilized binding component.

7. The method of claim 4, including after the contacting and cycling steps, again reversing the temperature of the polymer gel back through the polymer's critical solution temperature to desolvate the polymer gel and thereby expel said substance.

8. The method of claim 3 including, after the step of transferring, contacting the polymer gel/substance with a solution capable of releasing the immobilized complex from the polymer gel.

9. The method of claim 8 wherein said releasing solution contains a composition selected from the group consisting of added acids, bases, and enzymes.

10. The method of claim 1 wherein said binding component is a receptor and said substance is selected from the group consisting of hormones, vitamins, lectins, drugs and dyes.

11. The method of claim 11 wherein said binding component is an antibody and said substance is an antigen.

12. The method of claim 11 wherein said binding component is an enzyme and said desired substance is a substrate, inhibitor, coenzyme or cofactor.

13. The method of claim 11 wherein said binding component is selected from the group consisting of lectins, RNA, DNA (single or double stranded), ions, and stable free radicals and said desired substance is respectively selected from the group consisting of polysaccharides, glycoproteins, RNA or DNA complementary with said binding component, oligonucleotides, RNA or DNA binding proteins, chelators, ionophores, and free radicals.

14. The method of claim 1 wherein said binding component is selected from the group consisting of anions, polyanions, anion/cation pairs, electron donors (Lewis base), and proton acceptors (Bronsted base), and said desired substance is respectively selected from the group consisting of cations, polycations, polyanion/polycation complexes, electronic acceptors (Lewis acid), and proton donors (Bronsted acid).

15. The method of claim 1 wherein said polymer gel is characterized by lower critical solution temperature (LCST).

16. The method of claim 15 wherein the LCST polymer gel includes a polymer selected from the group consisting of N-substituted acrylamides or methacrylamides, hydroxy alkyl celluloses, polyoxazolidones, polyvinyl methyl ethers, polyethlyene oxide, polymethacrylic acid, and copolymers thereof.

17. The method of claim 16 wherein said polymer is N-substituted acrylamide or methacrylamide and includes N- or N,N-alkyl substituted substituents selected from the group consisting of methyl, ethyl, propyl, butyl, phenyl, pyrrolidine and pideridine.

18. The method of claim 16 wherein said polymer is a hydroxy alkyl cellulose selected from the group consisting of hydroxymethyl cellulose, hydroxypropyl cellulose, hydroxypropyl methyl cellulose, and copolymers thereof.

19. The method of claim 1 wherein said polymer gel is characterized by an upper critical solution temperature (UCST).

20. The method of claim 19 wherein the UCST polymer gel includes a polymer selected from the group consisting of polyacrylic acid and polyvinyl alcohol.

21. The method of claim 1 wherein said binding component is immobilized to said polymer gel via a spacer molecule.

22. The method of claim 1 wherein said binding component is immobilized to said polymer gel by conjugating said binding component to a monomer and subsequently copolymerizing with additional monomers and cross-linking agents.

23. A method for separating a desired substance from a solution, comprising:
   introducing a polymer gel, that is characterized by a critical solution temperature and having a pore structure selected to absorb said desired substance within the gel on the basis of size, into a solution containing said desired substance; and
   adjusting the temperature of the polymer gel/solution through the polymer's critical solution temperature thereby causing said gel to absorb the desired substance and separate it from the solution.

24. The method of claim 23 wherein said pore structure is determined by adjusting the composition and/or amount of cross-linking agent employed with the polymer to form the polymer gel.

25. The method of claim 23 wherein said pore structure is determined by adjusting the composition and/or amount of monomer employed to form the polymer gel.

26. The method of claim 23 wherein said pore structure is determined by adjusting the composition and/or amount of solvent employed to form the polymer gel.

27. The method of claim 23 wherein said pore structure is determined by adjusting the amount and/or composition of initiators employed to form the polymer gel.

28. The method of claim 23 wherein said pore structure is determined by adjusting the composition and/or amount of chain transfer agents employed to form the polymer gel.

29. The method of claim 23 including, after the step of adjusting, removing the polymer gel/substance from the solution.

30. The method of claim 23 including, after the step of adjusting the temperature, reversing the temperature of the polymer gel back through the polymer's critical solution temperature to expel smaller molecular weight solution components.

31. The method of claim 23 wherein said polymer is characterized by a lower critical solution temperature (LCST).

32. The method of claim 31 wherein the LCST polymer gel includes a polymer selected from the group consisting of N-substituted acrylamides or methacrylamides, hydroxy alkyl celluloses, polyoxazolidones, polyvinyl methyl ethers, polyethylene oxide, polymethacrylic acid, and copolymers thereof.

33. The method of claim 32 wherein said polymer is N-substituted acrylamide or methacrylamide and includes N- or N,N-alkyl substituted substituents selected from the group consisting of methyl, ethyl, propyl, butyl, phenyl, pyrrolidine and pideridine.

34. The method of claim 32 wherein said polymer is a hydroxy alkyl cellulose selected from the group consisting of hydroxymethyl cellulose, hydroxypropyl cellulose, hydroxypropyl methyl cellulose, and copolymers thereof.

35. The method of claim 23 wherein said polymer is characterized by an upper critical solution temperature (UCST).

36. The method of claim 35 wherein the UCST polymer gel includes a polymer selected from the group consisting of polyacrylic acid and polyvinyl alcohol.

37. A method for delivering a substance into a selected environment, comprising:
incorporating a desired substance into a polymer gel, characterized by a critical solution temperature having immobilized therein a binding component that is a binding partner of said desired substance, by binding said substance to said binding component thereby forming an immobilized complex; and
introducing said polymer gel/substance into a selected environment containing one or more agents capable of releasing said substance from said immobilized complex, thereby delivering said substance into the environment.

38. The method of claim 37 including, subsequent to the step of introducing, adjusting the temperature of the polymer gel through the polymer's critical solution temperature to cause the gel to deliver the desired substance into the environment.

39. The method of claim 37 wherein said agent is selected from the group consisting of acids, bases, salts, ionic detergents, non-ionic detergents, organic solvents and chaotropic agents.

40. The method of claim 37 wherein said agent is a compound having a greater affinity to bind the desired substance than said immobilized binding component.

41. The method of claim 37 wherein said binding component specifically binds with said substance.

42. The method of claim 41 wherein said binding component is a receptor and said substance is selected from the group consisting of hormones, vitamins, lectins, drugs and dyes.

43. The method of claim 41 wherein said binding component is an enzyme and said desired substance is a substrate, inhibitor, coenzyme or cofactor.

44. The method of claim 41 wherein said binding component is selected from the group consisting of lectins, RNA, DNA (single or double stranded), ions, and stable free radicals and desired substance is respectively selected from the group consisting of polysaccharides, glycoproteins, RNA or DNA complementary with said binding component, oligonucleotides, RNA or DNA binding proteins, chelators, ionophores, and free radicals.

45. The method of claim 37 wherein said polymer gel is characterized by lower critical solution temperature (LCST).

46. The method of claim 37 wherein said polymer gel is characterized by an upper critical solution temperature (UCST).

47. A method for selectively delivering a desired substance into an environment comprising:
incorporating a desired substance into a polymer gel characterized by a critical solution temperature and having a pore structure selected to absorb said desired substance within the gel on the basis of size;
introducing the polymer gel/substance into a selected environment; and
adjusting the temperature of the polymer gel/substance through the polymer's critical solution temperature to selectively deliver the desired substance into the environment.

48. The method of claim 47 wherein said pore structure is selected by adjusting the composition and/or amount of cross-linking agent employed with the polymer to form the polymer gel.

49. The method of claim 47 wherein said pore structure is selected by adjusting the composition and/or amount of monomer employed to form the polymer gel.

50. The method of claim 47 wherein said pore structure is selected by adjusting the composition and/or amount of solvent employed to form the polymer gel.

51. The method of claim 47 wherein said pore structure is selected by adjusting the amount and/or composition of initiators employed to form the polymer gel.

52. The method of claim 47 wherein said pore structure is selected by adjusting the composition and/or amount of chain transfer agents employed to form the polymer gel.

53. A method for selectively controlling a reaction within a particular environment containing a reactable substance, comprising:
introducing into the environment a polymer gel characterized by a critical solution temperature having immobilized therein a chemically or biochemically active component, said component being reactive with said substance when exposed to said substance; and
selectively adjusting the temperature of said polymer gel through the polymer's critical solution temperature such that said component is selectively exposed to said reactable substance within the environment, thereby providing control over said reaction.

* * * * *